US010039758B2

(12) United States Patent
Martchenko et al.

(10) Patent No.: US 10,039,758 B2
(45) Date of Patent: Aug. 7, 2018

(54) COMPOSITIONS AND METHODS FOR INHIBITING BACTERIAL AND VIRAL PATHOGENS

(71) Applicant: KECK GRADUATE INSTITUTE OF APPLIED LIFE SCIENCES, Claremont, CA (US)

(72) Inventors: Mikhail Martchenko, Claremont, CA (US); Leeor Zilbermintz, Encino, CA (US); William Leonardi, Rosemead, CA (US)

(73) Assignee: Keck Graduate Institute of Applied Life Sciences, Claremont, CA (US)

( * ) Notice: Subject to any disclaimer, the term of this patent is extended or adjusted under 35 U.S.C. 154(b) by 80 days.

(21) Appl. No.: 14/922,114

(22) Filed: Oct. 23, 2015

(65) Prior Publication Data

US 2016/0113920 A1 Apr. 28, 2016

Related U.S. Application Data

(60) Provisional application No. 62/068,500, filed on Oct. 24, 2014, provisional application No. 62/183,887, filed on Jun. 24, 2015.

(51) Int. Cl.

| | |
|---|---|
| ***A61K 31/4706*** | (2006.01) |
| ***A61K 31/131*** | (2006.01) |
| ***A61K 45/06*** | (2006.01) |

(52) U.S. Cl.

CPC ........ *A61K 31/4706* (2013.01); *A61K 31/131* (2013.01); *A61K 45/06* (2013.01)

(58) Field of Classification Search

CPC .......................... A61K 31/4704; A61K 31/131
USPC .......................................................... 514/313
See application file for complete search history.

(56) References Cited

U.S. PATENT DOCUMENTS

| | | | | |
|---|---|---|---|---|
| 3,549,751 | A | 12/1970 | McBride et al. | |
| 5,948,815 | A | 9/1999 | Fleiszig et al. | |
| 7,026,360 | B1 | 4/2006 | Festo | |
| 8,232,265 | B2 | 7/2012 | Rogers et al. | |
| 9,439,876 | B2 * | 9/2016 | Martchenko | A61K 31/131 |
| 2015/0196499 | A1 * | 7/2015 | Martchenko | A01N 33/04 514/663 |

(Continued)

FOREIGN PATENT DOCUMENTS

| | | |
|---|---|---|
| WO | WO 2004/030743 A2 | 4/2004 |
| WO | WO 2006/091610 A2 | 8/2006 |
| WO | WO 2007/098047 A2 | 8/2007 |

(Continued)

OTHER PUBLICATIONS

Kabara et al. (vol. 2(6); 1972 (PMC444344).*

(Continued)

*Primary Examiner* — Sabiha N Qazi

(74) *Attorney, Agent, or Firm* — Lewis Roca Rothgerber Christie LLP

(57) ABSTRACT

Compositions and methods including Amodiaquine (AQ) or N-Desethy Amodiaquine (DEAQ) are provided for treating, inhibiting, or preventing cathepsin B dependent pathogens and toxins in a host cell or infected subject. Compositions and methods also include AQ or DEAQ in combination with an antibiotic for more effective clearance of the pathogen and/or toxins.

7 Claims, 26 Drawing Sheets
(10 of 26 Drawing Sheet(s) Filed in Color)

(56) References Cited

U.S. PATENT DOCUMENTS

2016/0113920 A1* 4/2016 Martchenko ......... A61K 31/131
514/313

FOREIGN PATENT DOCUMENTS

| | | | |
|---|---|---|---|
| WO | WO 2012/041493 | A1 | 4/2012 |
| WO | WO 2013/001073 | A1 | 1/2013 |
| WO | WO 2014/100777 | A2 | 6/2014 |

OTHER PUBLICATIONS

Peter B. Madrid et al. (PLOS One, (vol. 8, Apr. 13, Issue 4, pp. 1-12, e60579).*

Zilbermintz et al. (Sci Rep. 2015; 5: 13476, pp. 1-21).*

Boonyasuppayakorn et al. (Antiviral Res. Jun. 2014; 106: 125-134).*

International Search Report for International Patent Application No. PCT/US2015/057257, dated Jan. 14, 2016. (12 pages).

Qiao et al., "The antimalarial amodiaquine causes autophagic-lysosomal and proliferative blockade sensitizing human melanoma cells to starvation- and chemotherapy-induced cell death" Authophagy, Dec. 2013, vol. 9, No. 12, pp. 2087-2102.

Mallea et al., "Alkylaminoquinolines inhibit the bacterial antibiotic efflux pump in multidrug-resistant clinical isolates", Biochemical Journal, 2003, vol. 376, pp. 801-805.

Ha et al., "Cathepsin B-mediated Autophagy Flux Facilitates the Anthrax Toxin Receptor 2-mediated Delivery of Anthrax Lethal Factor into the Cytoplasm", J. Biol. Chem, 2010, 285: 2120-2129.

Gnirss et al., "Cathepsins B and L activate Ebola but not Marburg virus glycoproteins for efficient entry into cell lines and macrophages independent of TMPRSS2 expression", 2012, *Virology*, 424:3-10.

Sanchez, "Analysis of Filovirus Entry into Vero E6 Cells, Using Inhibitors of Endocytosis, Endosomal Acidification, Structural Integrity, and Cathepsin (B and L) Activity", 2007, *J. Infect. Dis.* 196 Suppl 2:S251-258.

Lu et al., "EST-based genome-wide gene inactivation identifies ARAP3 as a host protein affecting cellular susceptibility to anthrax toxin", 2004, PNAS, vol. 101, No. 49, pp. 17246-17251.

Artenstein, Andrew W. et al.; "Chloroquine Enhances Surivival in *Bacillus anthracis* Intoxication"; Chloroquine-Enhanced Anthrax Survival; JID 2004:190; Nov. 1, 2004; pp. 1655-1660.

Comer, J.E. et al.; "Evaluation of the Protective Effects of Quinacrine Against *Bacillus anthracis* AMES"; Journal of Toxicology and Environmental Health, Part A; 69; 2006; pp. 1083-1095.

* cited by examiner

- Anthrax Toxin (LF+PA)
- Anthrax Toxin + 1.5 mg/kg Amodiaquine
- Anthrax Toxin + 3.0 mg/kg Amodiaquine
- Anthrax Toxin + 6.0 mg/kg Amodiaquine
- 6 mg/kg Amodiaquine

COMPOSITIONS AND METHODS FOR INHIBITING BACTERIAL AND VIRAL PATHOGENS

CROSS-REFERENCE TO RELATED APPLICATION(S)

The present application claims priority to and the benefit of U.S. Provisional Application Ser. No. 62/068,500 filed on Oct. 24, 2014 and U.S. Provisional Application Ser. No. 62/183,887 filed on Jun. 24, 2015, the entire contents of both of which are incorporated herein by reference.

BACKGROUND

Medical treatments generally target specific cellular functions of patients to cure or mitigate the effects of diseases. However, the strategy underlying treatment of an infectious disease treatment is to target the infecting pathogen. Inevitably, and not surprisingly, the targeting of pathogens has led to the emergence and spread of pathogens having mutational resistance to countermeasures. In recent years, such resistance has sparked interest in agents that target host functions that are exploited by pathogens. It has been shown that multiple pathogens or toxins that affect hosts by different mechanisms may use the same host pathways.

Numerous pathogens enter mammalian eukaryotic cells by exploiting cellular endocytosis. Among these pathogens are many with high rates of mortality or morbidity, including anthrax, smallpox, Ebola and Marburg's Disease. Some pathogens may exploit only the endocytic pathway, while others may exploit endocytosis in addition to other pathways. Still other pathogens are known to exploit endocytosis, but the specific type of pathway or pathways have not yet been identified.

Furthermore, some pathogens reproduce rapidly in mammals and also produce toxins that damage the host cells. Examples of such pathogens include *Bacillus* anthracis, *Clostridium botulinum, C. difficile*, and *Corynebacterium diphtheriae* (diphtheria). The treatment of such pathogens thus requires inhibition of cellular damage from the toxins as well as removal of the bacteria, which may be difficult in a subject having a compromised immune system.

SUMMARY

In some embodiments of the present invention, a method of inhibiting an endocytic pathogen or endocytic pathogen toxin in a host cell or in a subject includes administering Amodiaquine (AQ) or N-Desethyl Amodiaquine (DEAQ) to the host cell or the subject, where the endocytic pathogen is selected from *Bacillus anthracis, Clostridium difficile, Clostridium botulinum*, diphtheria, small pox, tuberculosis, or combinations thereof.

In some embodiments of the present invention, a method of inhibiting an endocytic pathogen or endocytic pathogen toxin in a host cell or in a subject includes administering Amodiaquine (AQ) or N-Desethyl Amodiaquine (DEAQ) to the host cell or the subject in combination with administration of an antibiotic. In some embodiments, the antibiotic is selected from Octodrine, vancomycin, clindamycin, cephaloridine, fidaxomicin, metronidazole, ciprofloxacin, doxycycline, erythromycin, penicillin, tetracycline, or combinations thereof. In some embodiments the combination is mixture for parenteral administration.

In some embodiments of the present invention, a composition for inhibiting an endocytic pathogen or endocytic pathogen toxin in a host cell or a subject includes Amodiaquine (AQ) or N-Desethyl Amodiaquine (DEAQ), and an antibiotic.

In some embodiments of the present invention, a method of inhibiting a cathepsin B dependent pathogen or cathepsin B dependent pathogen toxin in a host cell or in a subject includes administering Amodiaquine or N-Desethyl Amodiaquine to the host cell or the subject. In some embodiments, an antibiotic is also administered to the host cell or subject.

In some embodiments of the present invention, a cathepsin B dependent pathogen is selected from *Bacillus anthracis, Clostridium difficile, Clostridium botulinum*, diphtheria, tuberculosis, smallpox virus, SARS (severe acute respiratory syndrome) coronavirus, Venezuelan equine encephalitis virus, rabies virus, Junin virus, Chikungunya virus, and combinations thereof.

In some embodiments of the present invention, a composition for inhibiting a cathepsin B dependent pathogen or cathepsin B dependent pathogen toxins includes Amodiaquine (AQ) or N-Desethyl Amodiaquine (DEAQ). In some embodiments, the composition also includes an antibiotic.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
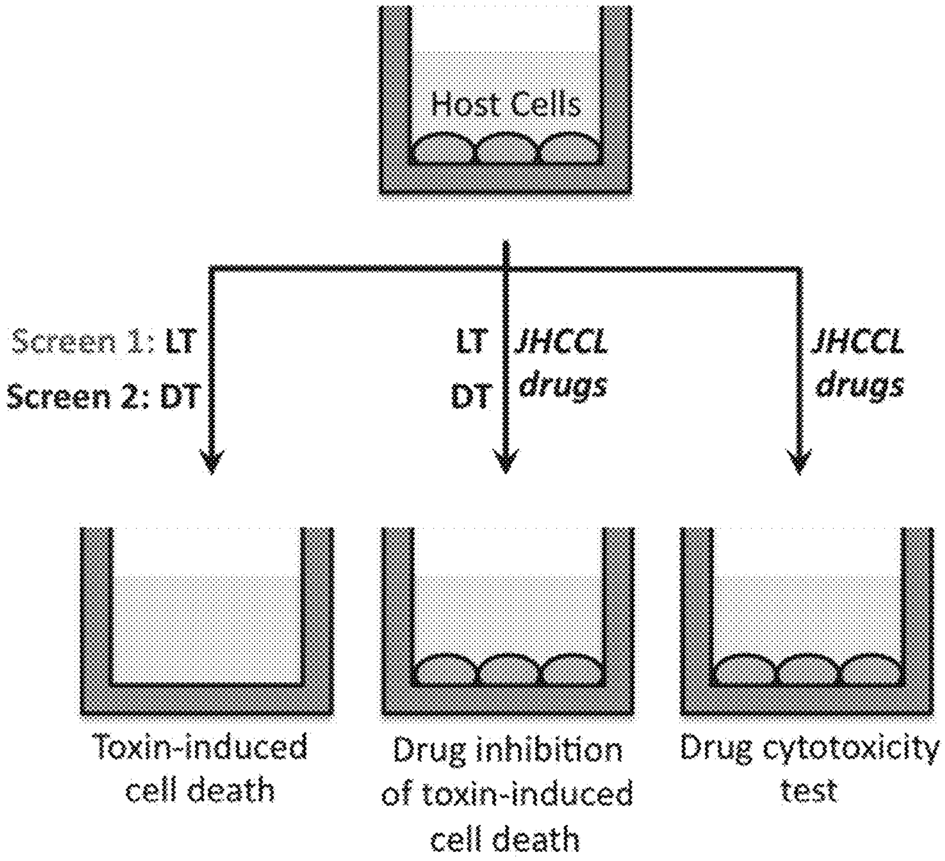
FIG. 1 is a schematic diagram of cellular screens using Johns Hopkins Clinical Compound Library (JHCCL) to identify drugs that reduce cellular lethality induced by anthrax lethal toxins (LT), which include lethal factor (LF) and protective antigen (PA) and diphtheria toxin (DT).
Figure 2:
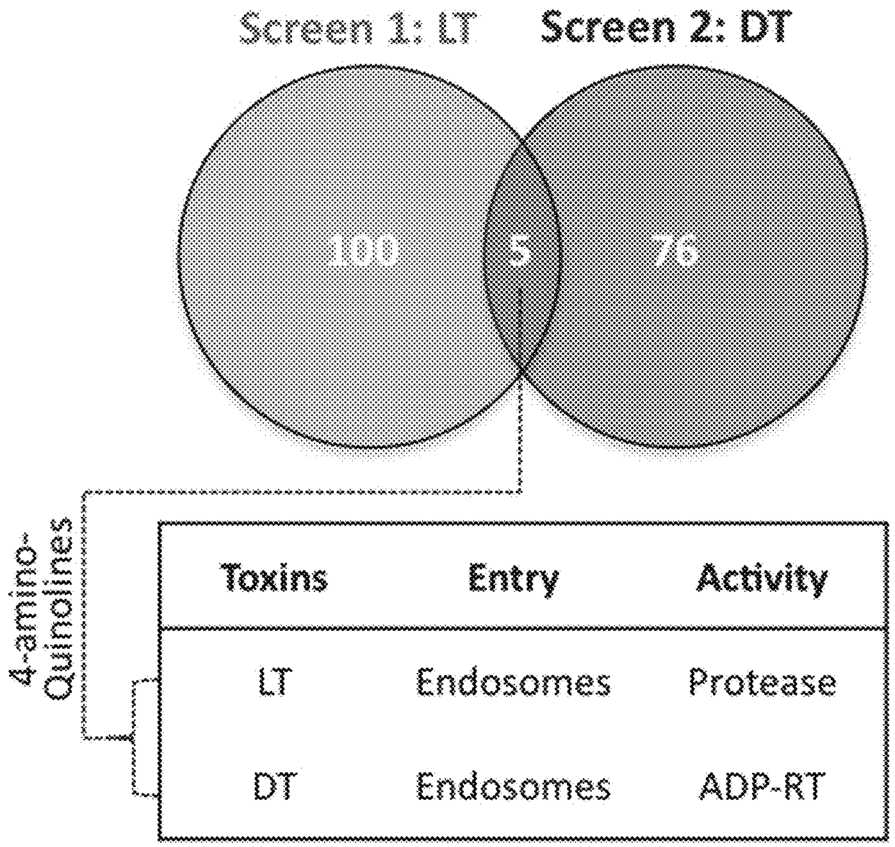
FIG. 2 is a schematic showing the distributions of inhibitors obtained in the screens depicted in FIG. 1, with a table showing the routes taken by toxins to enter into cellular cytoplasm (Endocytosis), as well as the enzymatic activities of toxins (Protease or ADP-rybosyltransferase (ADP-RT)).
Figure 3:
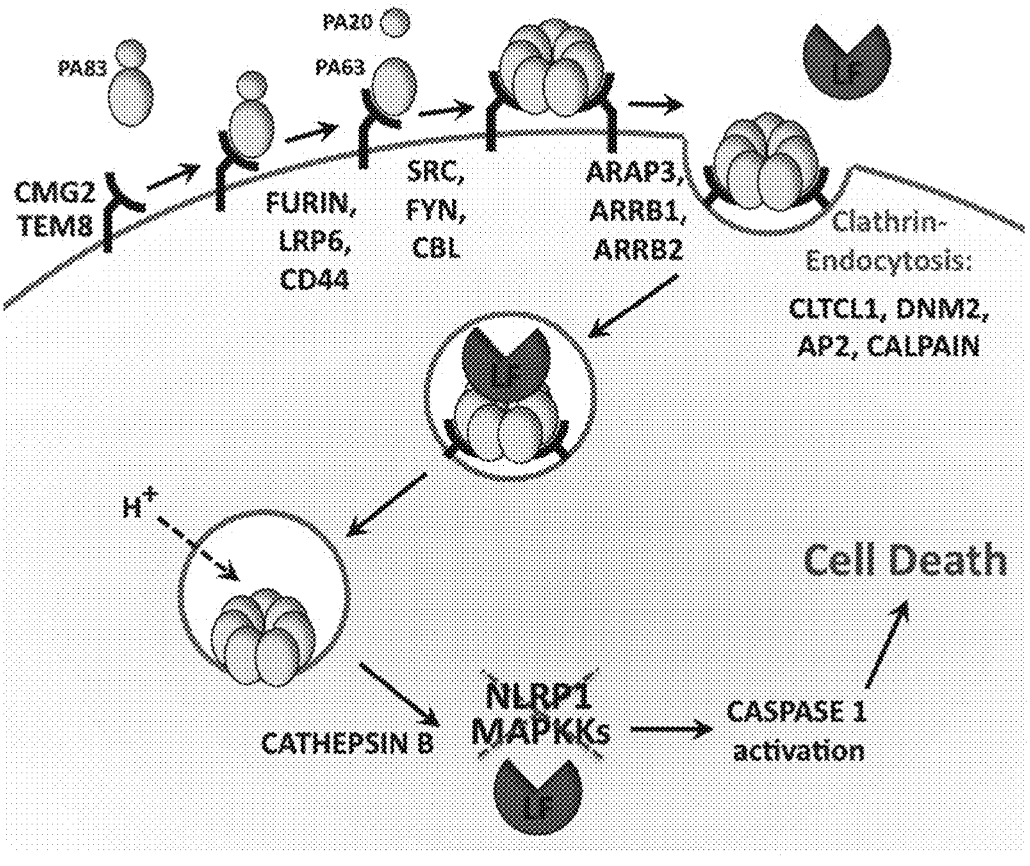
FIG. 3 is a schematic depiction of the host pathway that mediates the delivery of anthrax toxin into the cytoplasm, in which lethal factor (LF) and edema factor (EF) interact with a third *B. anthracis*-generated protein, protective antigen (PA), and the three host cell proteins, CMG2, TEM8, and ITGB 1, can serve as receptors for the bipartite PA/LF and PA/EF toxins, and where fifteen additional host proteins are known to assist PA binding and/or internalization, according to embodiments of the present invention.

Using a cell-based multiplex approach to screen a library of FDA-approved drugs for inhibition of disparately acting pathogens, Amodiaquine, which was previously used clinically as an antimalarial agent, is shown to inhibit both the detrimental effects of multiple bacterial toxins and the entry of Ebola and other viruses into host cells (FIGS. 1-2). The broad antipathogenic mechanism of action of Amodiaquine and its metabolite, N-desethyl-Amodiaquine, is the inhibition of the host protein, cathepsin B, located in the late endosome (FIG. 3). Accordingly, Amodiaquine and N-Desethyl Amodiaquine are capable of inhibiting cathepsin B-dependent pathogens that utilize the host cell's pH-dependent endosomal pathway leading to pyroptosis (i.e., host cell death).

As used herein, the term "pathogen" refers to a virus or bacteria, and may also include the "toxins of the pathogen." For example, inhibition of an endocytic pathogen includes inhibition of the pathogen and inhibition of the toxins of the pathogen.

Figure 7:
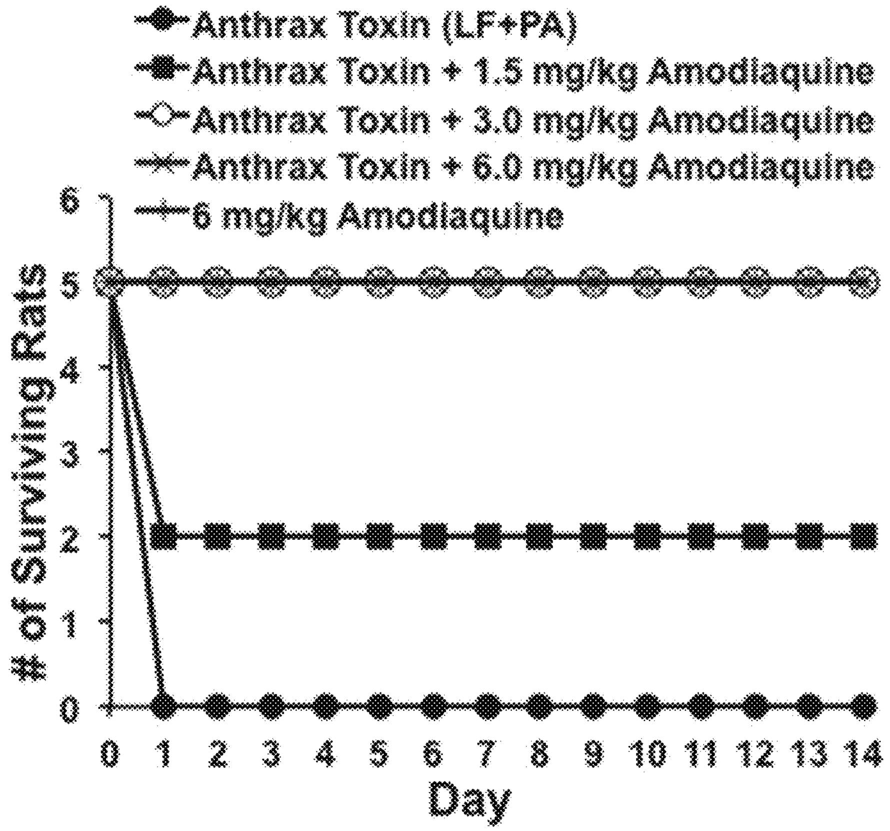
FIG. 7 is a graph showing percent survival of Sprague-Dawley rats given Amodiaquine alone at 6mg/kg or anthrax toxin cocktail (12 ug LF mixed with 40 ug PA) alone, or a combination of anthrax toxin cocktail with 1.5 mg/kg Amodiaquine, 3.0 mg/kg Amodiaquine, or 6.0 mg/kg Amodiaquine as indicated, according to embodiments of the present invention.

The term "prevent," and like terms, as used herein, refers to all activities that inhibit pathogenicity or retard pathogenesis of a pathogen infection by administering a composition according to embodiments of the present invention, which includes at least Amodiaquine (AQ) or N-Desethyl Amodiaquine (DEAQ), and optionally another composition as disclosed herein. That is, the term "prevent" refers to a lack of pathogenesis, or to inhibition of pathogenesis, including inhibition of pathogenic agents or toxins. For example, as shown in FIG. 7, all of the rats that received AQ (at 3.0 mg/kg) and anthrax toxins (12 ug LF mixed with 40 ug PA) survived, therefore evidencing that the administration of AQ prevented death of these rats when exposed to the reported level of anthrax toxin exposure. In contrast, rats only receiving anthrax toxins (12 ug LF mixed with 40 ug PA) and no AQ died.

As used herein, "treat," "treating," "treatment," and like terms refer to a method of reducing the effects of pathogenesis resulting from infection by a pathogen (e.g., a cathepsin B dependent pathogen), and refers to all activities to improve, alleviate or otherwise favorably change the symptoms resulting from an infection by a pathogen by administration of a composition that includes at least Amodiaquine (AQ) or N-Desethyl Amodiaquine (DEAQ), and optionally another composition, as described herein.

As used herein, "subject" includes, but is not limited to, animals, including humans. The subject may be a vertebrate, for example, a mammal. The term "subject" does not denote a particular age or sex. Thus, adult and newborn subjects, as well as fetuses, whether male or female, are included in the term "subject."

Figure 6A:
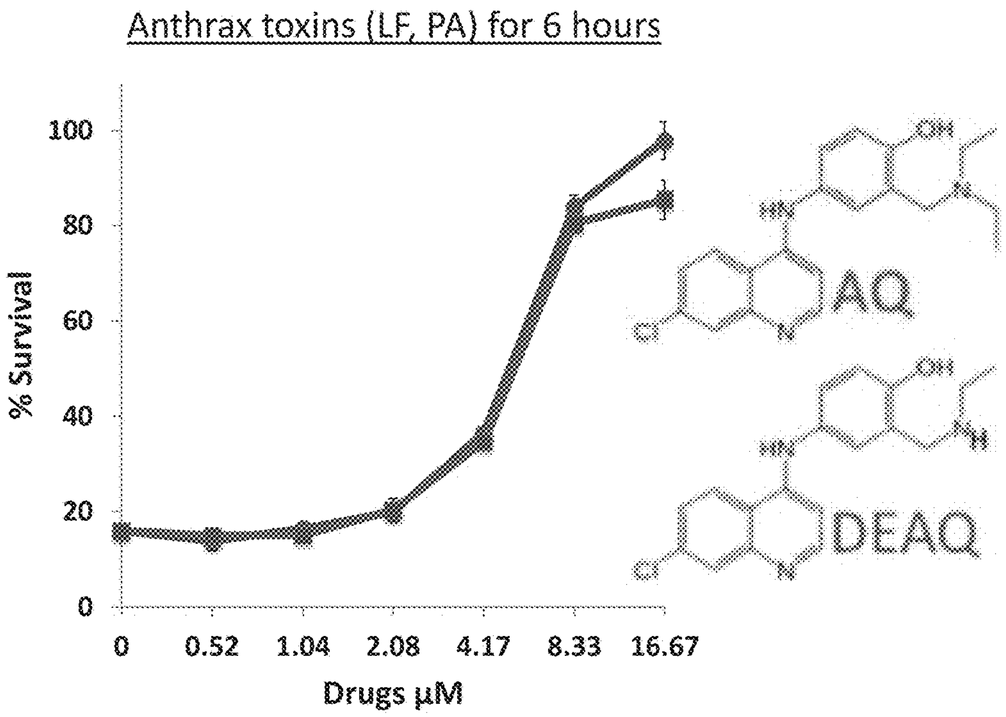
FIG. 6A is a graph showing the percent survival of RAW264.7 cells incubated with Amodiaquine (AQ) (red circles) or N-Desethyl Amodiaquine(DEAQ) (green squares) for 1 hour, followed by 6 hours of intoxication with anthrax toxins (500 ng/mL PA+500 ng/mL LF), according to embodiments of the present invention.
Figure 6B:
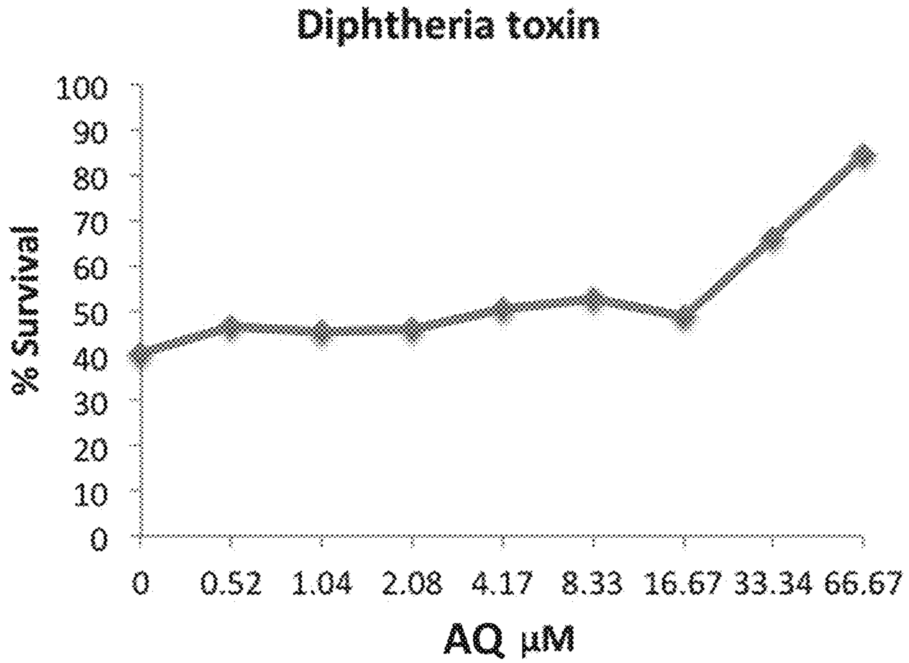
FIG. 6B is a graph showing the percent survival of human C32 cells incubated for 12 hours with 1 ug/mL diphtheria toxin in the presence of increasing amounts of Amodiaquine (AQ) (0.52 uM to 66.67 uM), according to embodiments of the present invention.
Figure 6C:
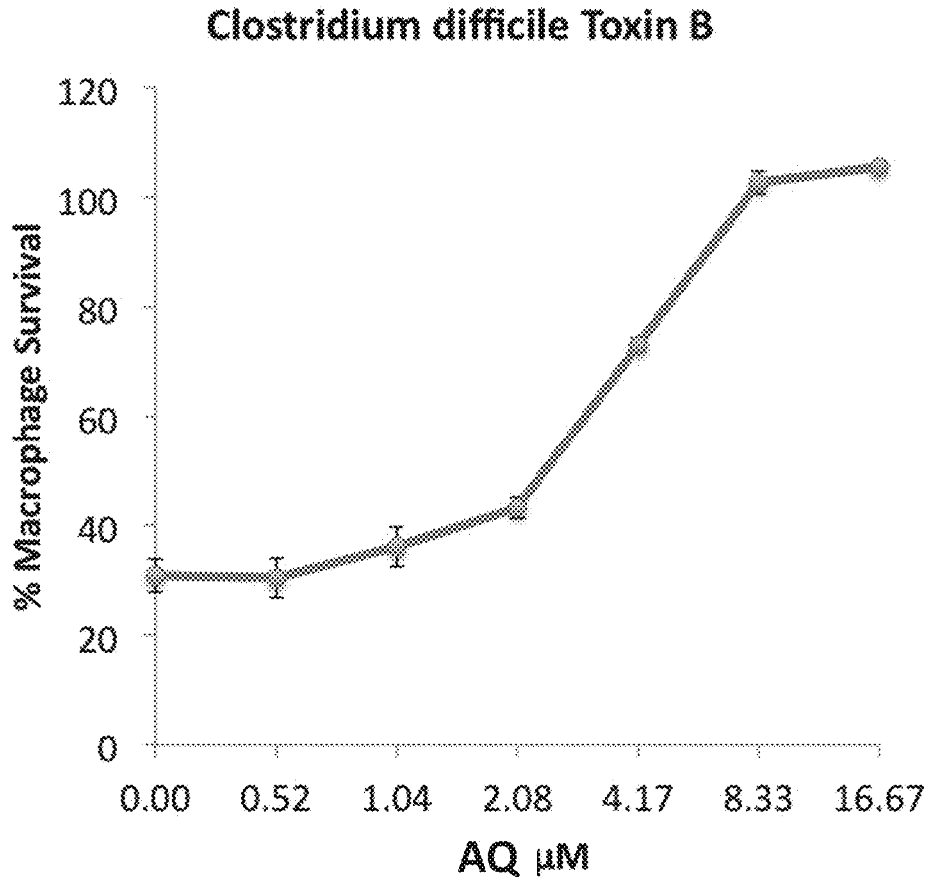
FIG. 6C is a graph showing the percent survival of RAW264.7 cells measured by an MTT assay in which the cells are pretreated with indicated amounts (0.52 uM to 16 uM) of Amodiaquine (AQ) for 1 hour, followed by incubation with 8.3 ug/mL of *Clostridium difficile* toxin B (CdTB) for 6 hours, according to embodiments of the present invention.
Figure 20B:
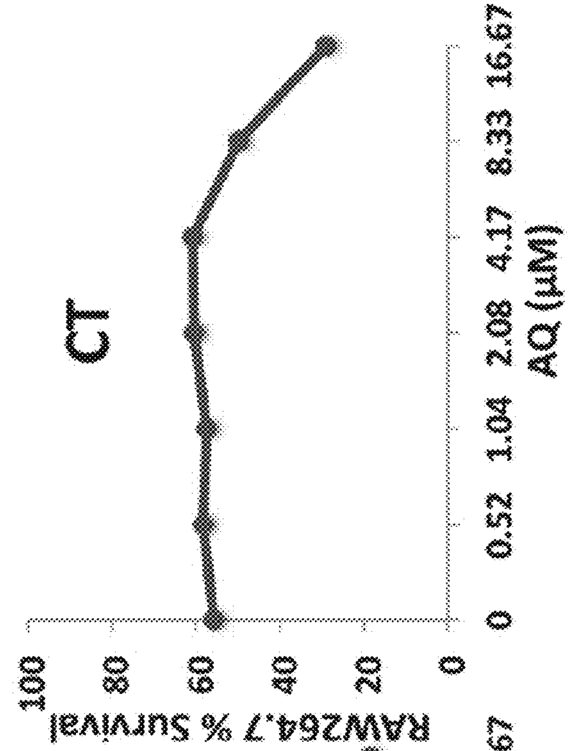
FIG. 20B is a graph showing the percent survival of RAW264.7 cells measured by an MTT assay in which the cells are pretreated with indicated amounts (uM) of Amodiaquine (AQ) for 1 hour, followed by incubation with 500 ng/mL of Cholera toxin (CT) for 6 hours, according to embodiments of the present invention.
Figure 20A:
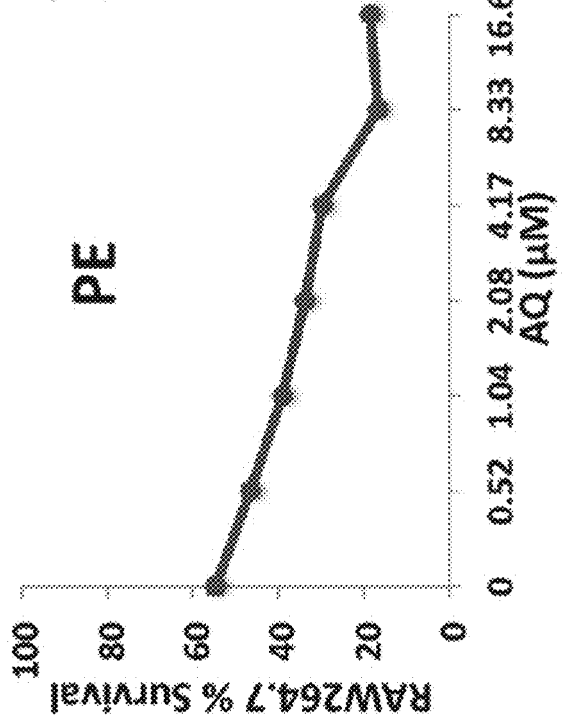
FIG. 20A is a graph showing the percent survival of RAW264.7 cells measured by an MTT assay in which the cells are pretreated with indicated amounts (uM) of Amodiaquine (AQ) for 1 hour, followed by incubation with 500 ng/mL of Pseudomonas aeruginosa Exotoxin A (PE) for 6 hours, according to embodiments of the present invention.
Figure 21:
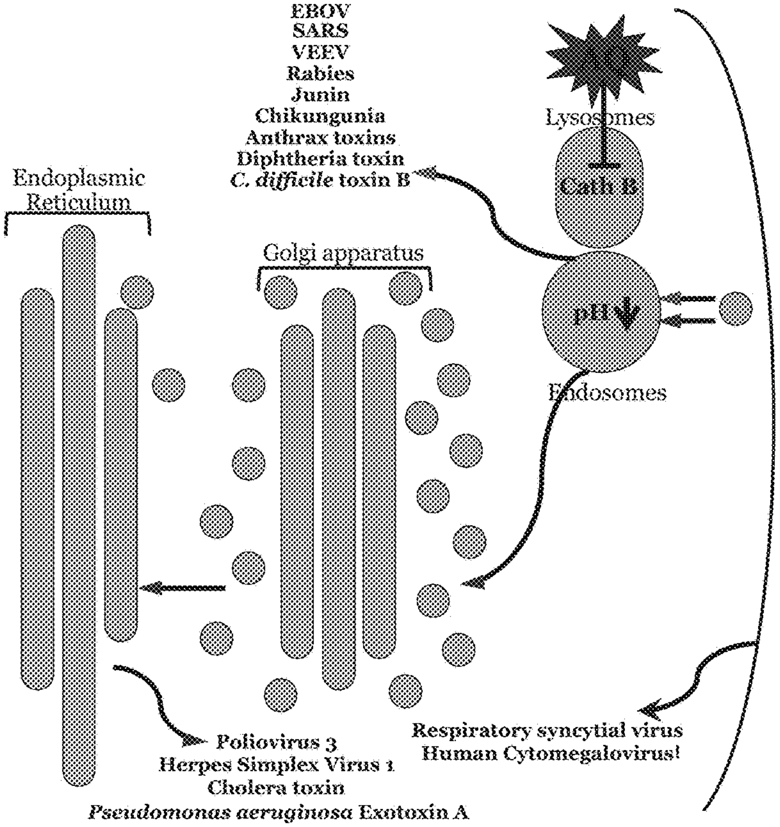
FIG. 21 is a schematic depiction of the mechanism of action of Amodiaquine (AQ) in which AQ reduces activities of pathogens that enter into the host cytoplasm from acidified endosomes by exploiting cellular cathepsin B as shown in the top pathway (shown in blue), according to embodiments of the present invention.

In some embodiments of the present invention, Amodiaquine or N-Desethyl Amodiaquine is administered to a cell or a subject infected with a cathepsin B-dependent pathogen, thereby inhibiting pathogen-related cell death and disease. For example, Amodiaquine (AQ) and N-Desethyl Amodiaquine (DEAQ) inhibit anthrax toxins lethal factor (LF) and protective antigen (PA) as shown in the increased survival of RAW264.7 macrophage cells in FIG. 6A. AQ is also shown to increase survival of human C32 cells infected with diphtheria toxin (FIG. 6B) and RAW264.7 macrophages infected with *Clostridium difficile* Toxin B (FIGS. 6C, 20A). As an example of in vivo analysis, AQ was shown to increase the survival of Sprague-Dawley rats infected with anthrax toxins (FIG. 7). Specifically, in FIG. 7, Amodiaquine at 1.5 mg/kg based on the weight of the rat increased the number of total rats surviving exposure to anthrax toxin, and Amodiaquine at 3.0 mg/kg and 6.0 mg/kg protected all of the rats that were exposed to anthrax toxin. The FDA-approved dose of Amodiaquine for the treatment of malaria is 10 mg/kg. Accordingly, in some embodiments of the present invention, a method of inhibiting a cathepsin B dependent pathogen in a host cell or in a subject, includes administering about 4.2 uM to about 70 uM, or about 1.5 mg/kg to about 10.0 mg/kg of Amodiaquine or N-Desethyl Amodiaquine to the host cell or the subject.

Protection by Amodiaquine was assayed in respective cells assays after exposure to multiple bacterial and viral pathogens as listed in Table 4. As shown, cells that were incubated with Amodiaquine showed significant protection from pathogenicity against Ebola Virus (EBOV), SARS corona virus, Venezuelan equine encephalitis virus, rabies virus, Junin virus, Chikungunya virus, and *Clostridium difficile* Toxin B (CdTB). These pathogens are cathepsin-B dependent pathogens and utilize the pH-dependent endosomal pathway.

In some embodiments of the present invention, the cathepsin B dependent pathogen is selected from *Bacillus anthracis, Clostridium difficile, Clostridium botulinum*, diphtheria, tuberculosis, smallpox virus, or combinations thereof.

In some embodiments of the present invention, the cathepsin B dependent pathogen is selected from *Bacillus anthracis, Clostridium difficile, Clostridium botulinum*, diphtheria, or combinations thereof.

In some embodiments of the present invention, the cathepsin B dependent pathogen is selected from *Bacillus anthracis, Clostridium difficile, Clostridium botulinum*, diphtheria, tuberculosis, smallpox virus, SARS coronavirus, Venezuelan equine encephalitis virus, rabies virus, Junin virus, Chikungunya virus, or combinations thereof.

Combination Compositions and Treatments

Some pathogens reproduce rapidly in mammals and also produce toxins that damage the host cells. Examples of such pathogens include *Bacillus anthracis, Clostridium botulinum, C. difficile*, and diphtheria. The treatment of such pathogens may thus include preventing or inhibiting toxin damage, and for patients whose immune systems cannot destroy the bacteria, an antibiotic that destroys the bacteria. Thus, for some subjects exposed to such pathogens, treatment that combines Amodiaquine or N-Desethyl Amodiaquine with an antibiotic may produce better clinical results than AQ or DEAQ alone. Non-limiting examples of antibiotics for this purpose include Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof.

In some embodiments of the present invention, a composition for treating or inhibiting a cathepsin B dependent pathogen, includes AQ or DEAQ and an antibiotic selected from Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof.

In some embodiments of the present invention, a composition includes AQ or DEAQ and an antibiotic in a mixture. The therapeutic amounts of antibiotics vary for each antibiotic and the therapeutic doses are known in the art and established for conventional tablets and/or parenteral (e.g., intravenous, intramuscular, subcutaneous) administration. The antibiotic dosage may vary depending on the weight of the subject and the severity of the infection. In some embodiments, the mixture of AQ or DEAQ and an antibiotic is a mixture for parenteral administration.

In some embodiments of the present invention, a composition includes AQ or DEAQ and an antibiotic selected from Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof in a mixture prepared for parenteral administration.

In some embodiments of the present invention, a composition includes a dose of about 1.5 mg/kg to about 10.0 mg/kg of Amodiaquine or N-Desethyl Amodiaquine in combination with Octodrine (6-methylheptan-2-amine), vancomycin, clindamycin, cephaloridine, fidaxomicin, metronidazole, ciprofloxacin, doxycycline, erythromycin, penicillin, tetracycline or combinations thereof. In some embodiments, a composition includes a parenteral dose (e.g., IV dose) of about 1.5 mg/kg to about 10.0 mg/kg of Amodiaquine or N-Desethyl Amodiaquine and a parenteral dose (e.g., IV dose) of about 1.5mg/kg to about 50 mg/kg Octodrine (6-methylheptan-2-amine). In some embodiments, the IV dose of Octodrine is about 4 to about 50 mg/kg.

Octodrine is disclosed as an antibiotic against gram-negative and gram-positive bacteria in U.S. Patent Publication No. 2015/0196499, Martchenko et al., Method of Treating Microbial Infections, filed Jan. 13, 2014, the entire content of which is incorporated herein by reference.

In some embodiments of the present invention, a method of treating, inhibiting, or preventing *Bacillus anthracis, Clostridium difficile, Clostridium botulinum*, diphtheria, tuberculosis, smallpox virus, SARS (severe acute respiratory syndrome) coronavirus, Venezuelan equine encephalitis virus, rabies virus, Junin virus, Chikungunya virus, or combinations thereof includes administering Amodiaquine or N-Desethyl Amodiaquine in combination with an antibiotic selected from Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof.

In some embodiments of the present invention, a method of treating, inhibiting, and/or preventing *Bacillus anthracis, Clostridium difficile, Clostridium botulinum*, and diphtheria and related toxins, includes administering Amodiaquine or N-Desethyl Amodiaquine in combination an antibiotic selected from Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof.

In some embodiments of the present invention, a method of treating, inhibiting, and/or preventing *Clostridium difficile* and its toxins in a host cell or in a subject, includes administering to the host cell or the subject about 4.2 uM to about 70 uM or about 1.5 mg/kg to about 10.0 mg/kg of Amodiaquine or N-Desethyl Amodiaquine in combination with an antibiotic selected from Octodrine (6-methylheptan-2-amine), vancomycin, clindamycin, cephaloridine, fidaxomicin, metronidazole, ciprofloxacin, doxycycline, erythromycin, penicillin, or tetracycline.

In some embodiments of the present invention, a method of treating, inhibiting, and/or preventing *Clostridium difficile* and its toxins in a host cell or in a subject, includes administering to the host cell or the subject about 4.2 uM to about 70 uM or about 1.5 mg/kg to about 10.0 mg/kg of Amodiaquine or N-Desethyl Amodiaquine in combination with Octodrine (6-methylheptan-2-amine). In some embodiments, a parenteral does (e.g., IV dose) of the Octrodrine is a dose of about 1.5 mg/kg to about 50 mg/kg Octodrine (6-methylheptan-2-amine). In some embodiments, the parenteral dose of Octodrine is about 4 to about 50 mg/kg.

For inhibition of cathepsin B dependent pathogens and their toxins in a subject, pathogenesis may be more effectively treated with Amodiaquine or N-Desethyl Amodiaquine in combination with an inhibitor of endocytosis. Additionally, subjects infected with multiple pathogens or a pathogen capable of utilizing the cathepsin B dependent pathway and a cathepsin B independent pathway may be treated with AQ or DEAQ in combination with an inhibitor of endocytosis. In some embodiments of the present invention, a composition for treating a subject infected with a cathepsin B dependent pathogen includes Amodiaquine or N-Desethyl Amodiaquine combined with a caveolin pathway inhibitor. Non-limiting examples of inhibitors of the caveolin pathway include Genistein and Nystatin. In some embodiments, in combination with AQ or DEAQ, Genistein may be administered to a subject at a dose of about 5-15 mg/kg/day up to high doses of about 150 mg/kg/day. In some embodiments, in combination with AQ or DEAQ, Nystatin is administered to a subject at a dose of about 20,000 up to about 400,000 units of an oral suspension up to about 4 times daily.

Severe infections caused by *Clostridium difficile* are often due to antibiotics that have killed other (often beneficial) bacteria, but leave the *C. difficile* bacteria untouched. Thus, treating *C. difficile* often requires suppressing the *C. difficile* bacteria while allowing the other bacteria to regrow. Such treatments include providing beneficial intestinal microbes (e.g., bacteria) to the subject. For example, these treatments may include introducing specific probiotics (e.g., *Saccharomyces boulardii* and *Lactobacillus* species), providing a fecal microbiota capsule, or administering a fecal microbiota transplantation (FMT). Combining microbes or probiotics in combination with Amodiaquine or N-Desethyl Amodiaquine may suppress the pathogenicity of *C. difficile*, while allowing the beneficial bacteria to rebuild in the subject's or patient's body.

In some embodiments of the present invention, a kit for treating *C. difficile* includes Amodiaquine or N-Desethyl Amodiaquine and the microbes of gut microbiota, for example, a fecal microbiota capsule and/or a probiotic such as *Saccharomyces boulardii* and/or *Lactobacillus*. In some embodiments, a kit for treating *C. difficile* includes a composition of Amodiaquine or N-Desethyl Amodiaquine mixed with an antibiotic as disclosed herein (e.g., Octodrine), and microbes of gut microbiota, for example, a fecal microbiota capsule and/or a probiotic such as *Saccharomyces boulardii* and/or *Lactobacillus*.

Administration of the AQ or DEAQ Composition

As used herein, the term "parenteral administration" and "administered parenterally" means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically," "peripheral administration" and "administered peripherally" as used herein mean the administration of a compound, drug or other material other than directly at a site of infection, such that it enters a system of the subject (e.g., the circulatory system, the respiratory system, or through the skin) and, thus, is subject to metabolism and other like processes.

As used herein, the terms "administering" and "introducing" are used interchangeably and refer to the placement of the pharmaceutical composition including an AQ or DEAQ composition according to some embodiments of the present invention, into a living organism or cells thereof by a method or route which results in at least partial localization of the AQ or DEAQ at a desired site.

In the preparation of pharmaceutical doses of the AQ or DEAQ composition for oral administration, the composition may be mixed with solid, powdered ingredients, such as lactose, saccharose, sorbitol, mannitol, starch, arnylopectin, cellulose derivatives, gelatin, and/or another suitable ingredient, as well as with disintegrating agents and lubricating agents such as magnesium stearate, calcium stearate, sodium stearyl fumarate and/or polyethylene glycol waxes. The mixture may then be processed into granules or pressed into tablets.

The following Examples are presented for illustrative purposes only, and do not limit the scope or content of the present application.

EXAMPLES

Example 1

Screening of FDA approved drugs for inhibitors of toxin-induced cell death. In a systematic effort to identify candidates for repurposing drugs as broad-spectrum, host-oriented, anti-toxin countermeasures, the Johns Hopkins Clinical Compound Library (JHCCL) of 1,581 agents (agents previously approved as drugs by the U.S. Food and Drug Administration) were screened for the ability to reduce lethality of RAW264.7 and C32 cells treated either with *Bacillus anthracis* lethal toxin or diphtheria toxin (FIG. 1). These toxins were chosen because the mechanisms underlying their pathogenicity are well understood and are disparate to each other.

Between 50 and 70 percent of cells used for these assays normally undergo cell death, as determined by MTT (3-(4, 5-dimethylthiazol-2-yl)-2,5-diphenyltetrazolium bromide) assay, within 6 and/or 24 hours of exposure to anthrax lethal toxin and diphtheria toxin respectively, under the experimental conditions employed. A "hit" in this screen was defined as an event where cells exposed to a compound at a concentration of 16 μM increased cell survival by at least 16 standard deviations (approximately 1% hit rate) above the survival of control cells treated with either toxin, but is not cytotoxic to cells in the absence of toxins. Events defined as "multiplex hits" interfered with cell killing by both of the toxins (FIG. 2). Five multiplex hits were identified and were tested further.

Anthrax toxin and diphtheria toxin enter the cytoplasm from acidified endosomes. Whereas diphtheria toxin is an ADP ribosyl transferase, anthrax toxin is a protease that cleaves host MAPKK (FIG. 3). To identify agents that inactivate host proteins exploited by toxins, hits that inhibit the mechanistically differently acting anthrax and diphtheria toxins were selected. In order to elucidate host-targets inhibited by these drugs only anthrax toxin was used, as the host cellular pathway that delivers the anthrax toxin into the cytoplasm is one of the best understood pathways (FIG. 3). Anthrax lethal toxin is an exotoxin protein complex consisting of protective antigen (PA) and lethal factor (LF), which act collectively to damage the host cell. PA is an 83 kDa cellular receptor-binding protein (PA83), and the combination of PA with LF is cytotoxic. LF is a 91 kDa zinc metalloprotease that cleaves the N-terminal substrate docking site of the mitogen-activated protein kinase kinases (MAP2K), preventing the passage of signals in the ERK1/2, p38, and c-Jun N-terminal kinase pathways. Intoxication of a cell begins when PA83 binds to host cellular receptors, capillary morphogenesis protein 2 (CMG2), tumor endothelial marker 8 (TEM8), or integrin beta 1 (ITGB1). Once bound, host furin cleaves a 20 kDa fragment from the N-terminus of PA83, thus activating the 63 kDa protein, PA63. Following activation, PA63 forms a heptamer and binds LF. The toxin undergoes clathrin-mediated endocytosis and a decrease in endosomal pH induces the formation of an endosomal membrane PA channel, by which LF translocates into the cytosol before PA pores are transported to lysosomes for rapid degradation. PA has been shown to induce the process of autophagy, whereby autophagosomes encapsulate endosomes and facilitate the delivery of LF into the cytoplasm. A lysosomal protein, cathepsin B, is necessary for the autophagic flux, whereby LF is delivered from the intralumenal vesicles of the autophagosome-encapsulated multivesicular late endosomes into the cytoplasm through a back fusion process.

Figure 4A:
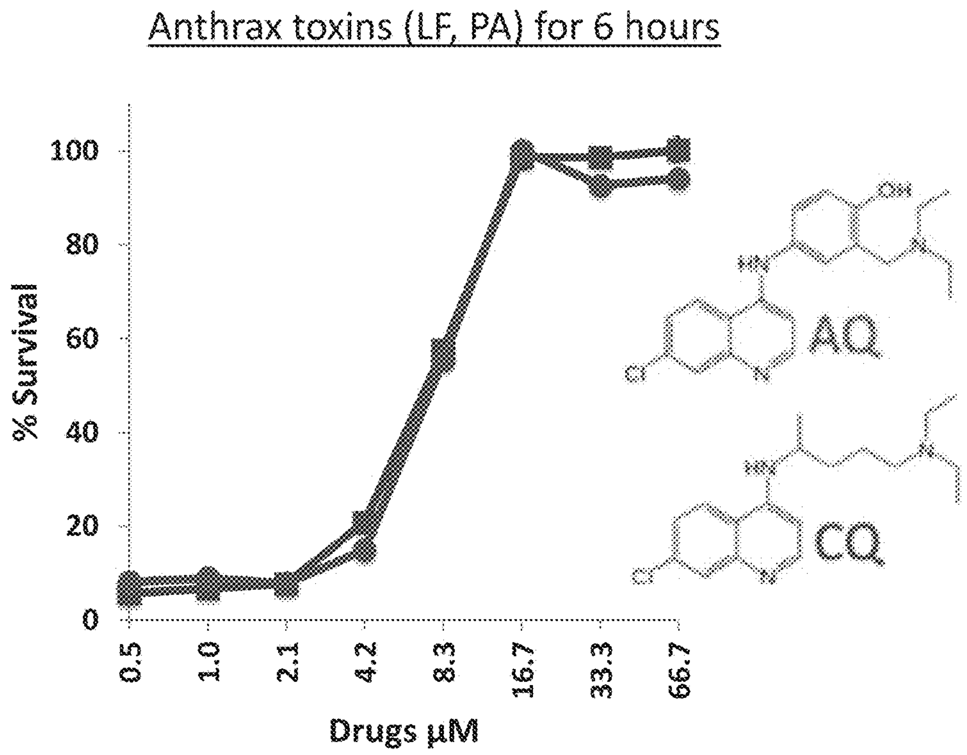
FIG. 4A is a graph showing percent of surviving RAW264.7 cells relative to RAW264.7 cells not treated with drugs for the doses (uM) as indicated for Amodiaquine (red circles) or Chloroquine (blue squares) for 1 hour, followed by 6 hours intoxication with 500 ng/mL PA+500 ng/mL LF toxins, according to embodiments of the present invention.
Figure 4B:
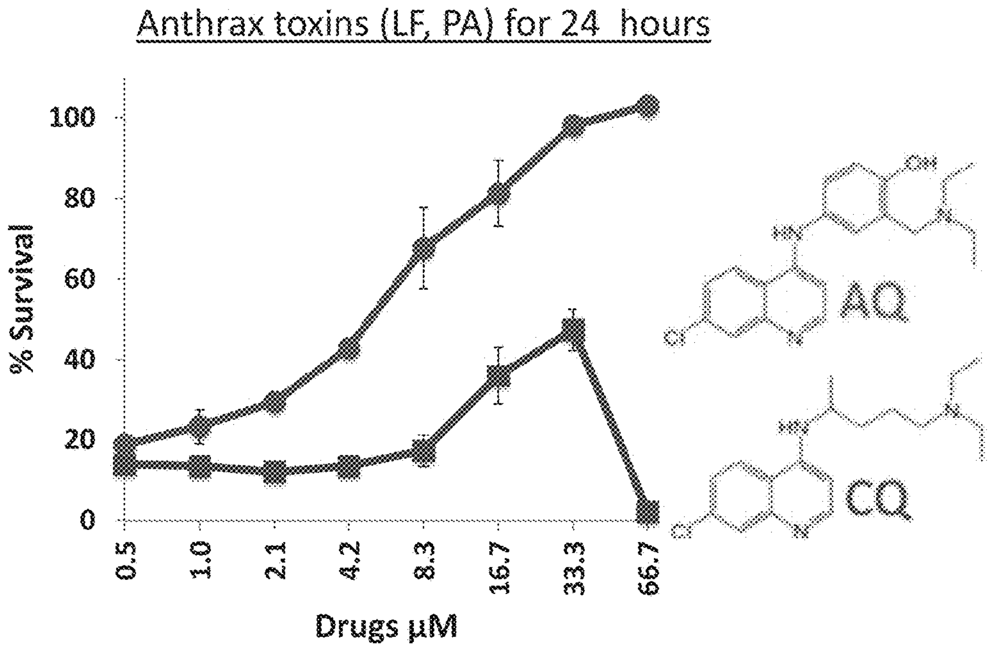
FIG. 4B is a graph showing percent of surviving RAW264.7 cells relative to RAW264.7 cells not treated with drugs for the doses (uM) as indicated for Amodiaquine (red circles) or Chloroquine (blue squares) for 1 hour, followed by 24 hours intoxication with 500 ng/mL PA+500 ng/mL LF toxins, according to embodiments of the present invention.
Figure 5A:
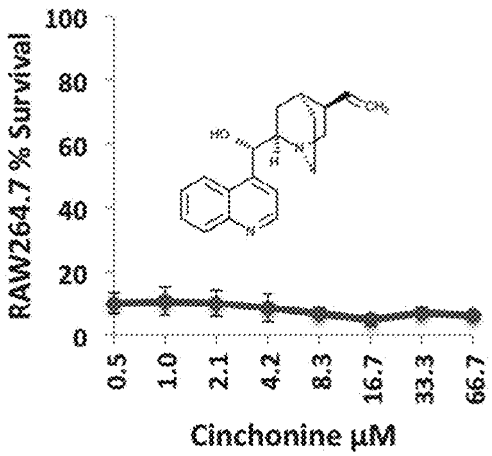
FIG. 5A is a graph showing the percent survival of RAW264.7 cells using an MTT assay, in which the RAW264.7 cells were pretreated with Cinchonine at the indicated concentrations (uM) for 1 hour, followed by treatment with anthrax toxins (500 ng/mL PA+500 ng/mL LF) for 6 hours, according to embodiments of the present invention.
Figure 5B:
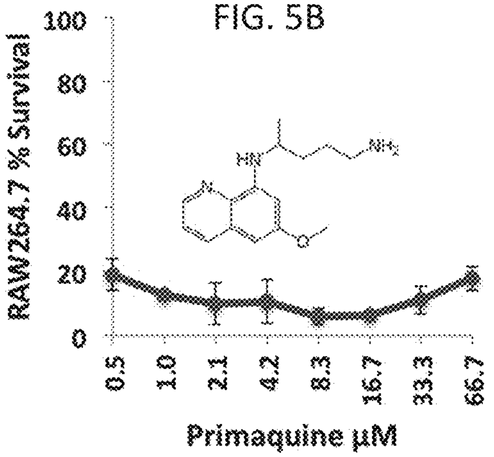
FIG. 5B is a graph showing the percent survival of RAW264.7 cells using an MTT assay, in which the RAW264.7 cells were pretreated with Primaquine at the indicated concentrations (uM) for 1 hour, followed by treatment with anthrax toxins (500 ng/mL PA+500 ng/mL LF) for 6 hours, according to embodiments of the present invention.
Figure 5C:
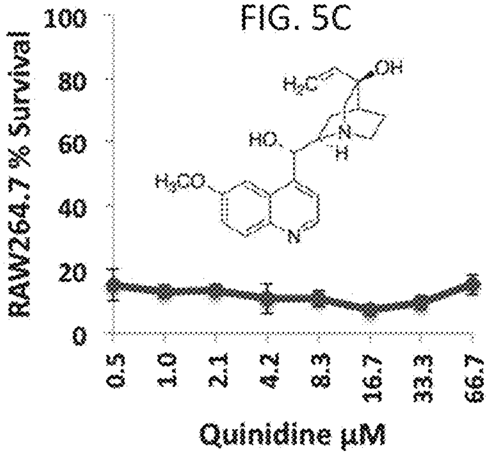
FIG. 5C is a graph showing the percent survival of RAW264.7 cells using an MTT assay, in which the RAW264.7 cells were pretreated with Quinidine at the indicated concentrations (uM) for 1 hour, followed by treatment with anthrax toxins (500 ng/mL PA+500 ng/mL LF) for 6 hours, according to embodiments of the present invention.

It was observed that out of five compounds that inhibited anthrax and diphtheria toxins, two compounds were structurally related 4-amino-quinolines, Chloroquine and Amodiaquine. Two anti-malarial drugs, Chloroquine (CQ) and Amodiaquine (AQ), were observed to completely protect host cells against anthrax toxin killing in 6-hours toxin killing assay (FIG. 4A). However, our assay showed that unlike AQ, CQ only has a moderate ability to protect cells against LF-PA mediated 24-hours killing (FIG. 4B). Interestingly, none of the other quinoline-containing antimalarial compounds, Cinchonine, Primaquine, and Quinidine, from JHCCL were active (FIGS. 5A, 5B, 5C).

Example 2

Amodiaquine and its metabolite are potent inhibitors of LF-PA induced death in vitro and in vivo. After oral administration, AQ is rapidly absorbed and undergoes fast and extensive metabolisation by hepatocytes' cytochrome p450 enzyme to the AQ metabolite, Desethyl-Amodiaquine (DEAQ), the main active metabolite of AQ. The ability of DEAQ to reduce anthrax toxin mediated cellular killing was tested, and it was observed that just like AQ, DEAQ was able to reduce toxin-mediated cytotoxicity with an EC50 of 5 μM (FIG. 6A). Since AQ and its metabolite, DEAQ, protected host cells against anthrax toxin killing, the efficacy of AQ was evaluated as a therapeutic agent during anthrax toxin intoxication in Sprague-Dawley rats. Animals were injected intravenously with a lethal dose of anthrax toxin (LD100) and were intravenously co-injected with AQ at 1.5, 3.0, or 6.0 mg/kg. The AQ doses were selected based on the FDA approved AQ dose of 10 mg/kg. Animals that received a lethal dose of anthrax toxin without AQ all died within 90 minutes post intoxication (FIG. 7). While the administration of AQ at 1.5 mg/kg saved 40% of the rats, all of the animals in that group displayed classical signs of having undergone a toxin challenge, such as ataxia, lethargy, hyperpnea, and tachypnea. Rats that were challenged with anthrax toxin and treated with AQ at 3.0 and 6.0 mg/kg all survived without displaying toxin-associated symptoms (FIG. 7).

Example 3

Figure 8:
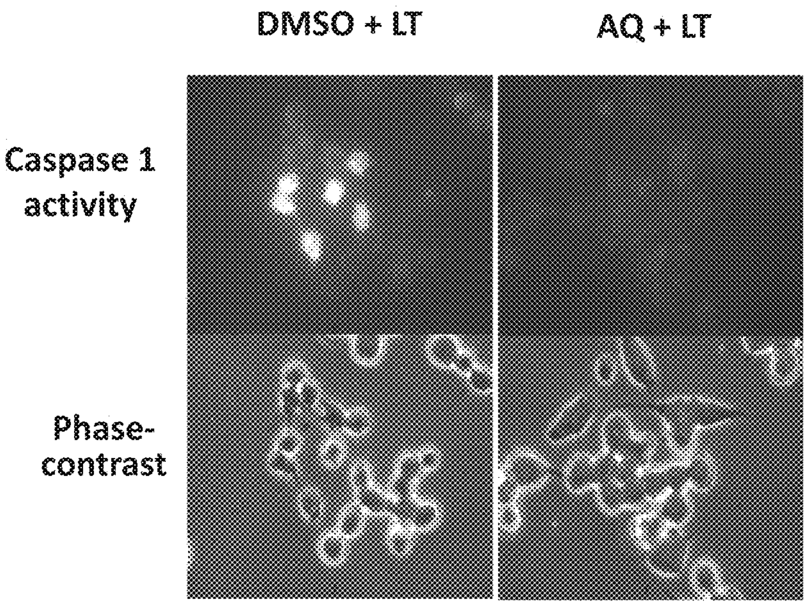
FIG. 8 shows fluorescent microscopic images of RAW264.7 cells incubated with 16 uM Amodiaquine (AQ) or DMSO as control for 1 hour prior to addition of 500 ng/mL PA+LF (LT) for 2 hours, followed by the incubation of active caspase-1 binding fluorescent probe, FLICA for 1 hour, followed by fluorescence microscopy analysis, according to embodiments of the present invention.

Amodiaquine Inhibits Cytosolic Entry of LF. In order to identify the step at which AQ inhibits LF-PA-mediated lethality, the processes that mediate the cellular entry of this toxin and toxin-induced pyroptosis were assessed in the presence and in the absence of AQ. Caspase-1 activation, which occurs late in LF-PA intoxication, was monitored using a fluorescent probe, FLICA. This probe specifically binds to active caspase-1. While high levels of caspase-1 activity were observed upon LF-PA treatment in the absence of AQ, active caspase-1 was not detected in AQ-treated cells that were challenged with anthrax toxin (FIG. 8). This result shows that AQ inhibits cytotoxicity upstream of caspase-1 activation.

Figure 9:
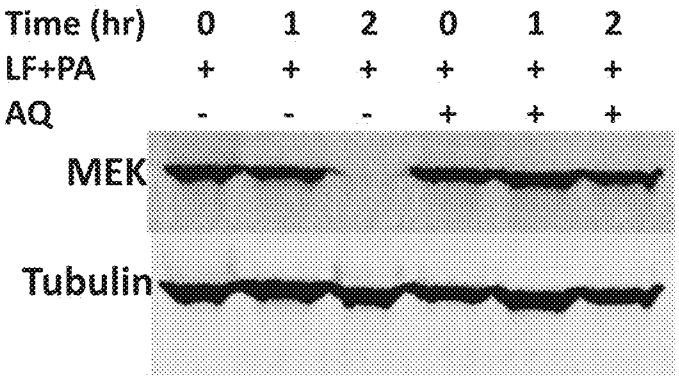
FIG. 9 is an image of a Western immunoblot of cell lysates from RAW264.7 cells incubated with (+) Amodiaquine (AQ) or without (−) (DMSO alone) for 1 hour prior to addition of vehicle control or 1 ug/mL PA+LF anthrax toxins for 1 or 2 hours, as indicated, after which cells were lysed and immunoblotted with a MEK-2-specific antibody with tubulin as a loading control, according to embodiments of the present invention.

Activation of caspase-1 by LF is a late step in pyroptosis, and depends on LF catalytic activity. To determine whether AQ blocks proteolysis of cellular MAPKKs by LF, the cleavage of MEK2 by immunoblotting was assessed. While MEK2 was cleaved in LF-PA treated RAW264.7 cells, treatment with AQ completely prevented this effect (FIG. 9). These results show that AQ inhibits either cytotoxicity upstream of MAPKK cleavage or blocks LF directly.

Figure 10A:
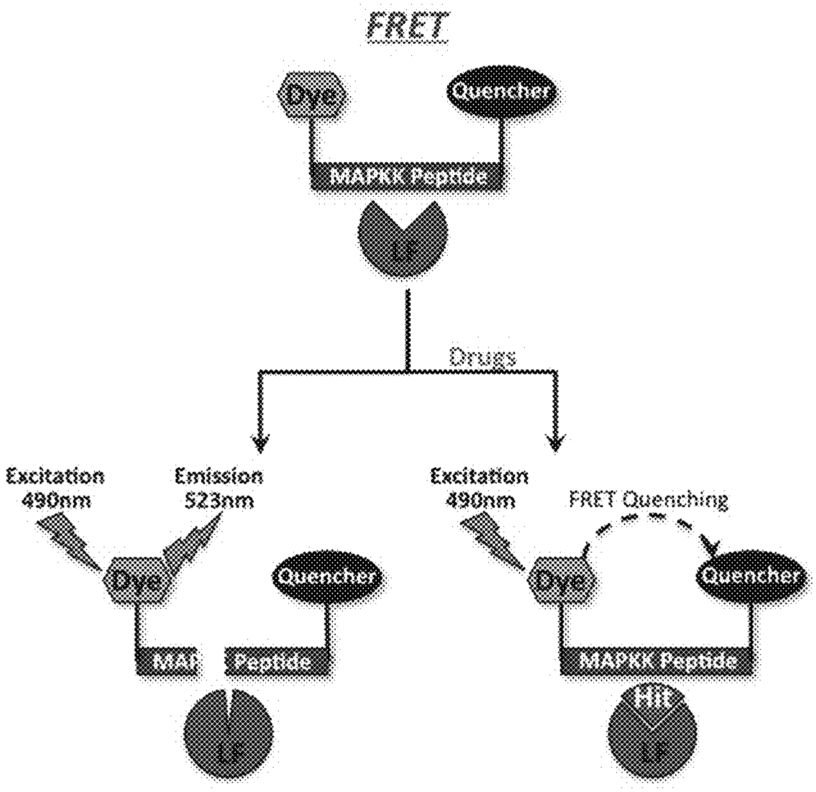
FIG. 10A is a schematic showing the mechanism for Fluorescence Resonance Energy Transfer (FRET) analysis using labeled MAPKK peptide to assess if a drug inhibits the proteolytic activity of LF toxin, which would thereby quench the fluorescence of the dye conjugated to MAPKK.
Figure 10B:
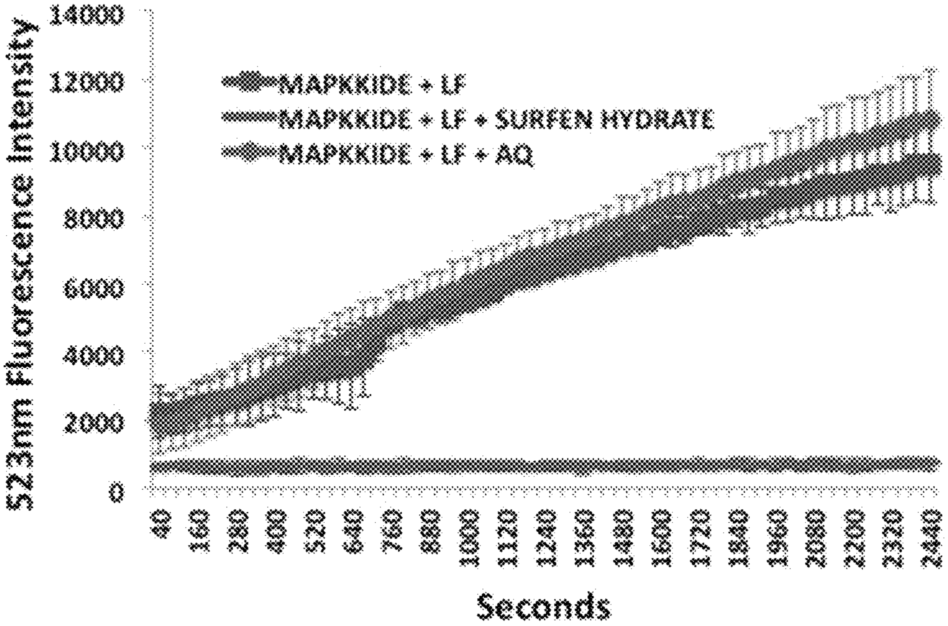
FIG. 10B is a graph showing fluorescence intensity at 523 nm over time (seconds) of a FRET assay as depicted in FIG. 10A, in which fluorescently labeled MAPKK peptide (MAPKKIDE) and LF toxin are shown in red; MAPKKIDE, LF toxin, and surfen hydrate (a known LF inhibitor) are shown in green; and MAPKKIDE, LF toxin, and Amodiaquine (AQ) are shown in blue, according to embodiments of the present invention.

In order to test whether AQ inhibits the enzymatic activity of LF, a Fluorescence Resonance Energy Transfer (FRET) based assay was used, in which an MEK2 peptide containing a cleavage site for LF with a fluorogenic DABCYL group at the N-terminus and FITC quenching group at the C-terminus was used as LF substrate for in vitro assays. After cleavage by LF, the fluorescence emitted by the DABCYL increased (FIG. 10A). The ability of AQ to inhibit the proteolytic activity of LF at 100 μM using FRET was tested. In the presence of a known small molecule inhibitor of LF, surfen hydrate, no emission at 523 nm was observed (FIG. 10B). In the absence of any chemical inhibitor, LF cleaved MAPKK peptide, and the fluorescence emission was observed (FIG. 10B). A similar emission at 523 nm was observed when LF was able to cleave MAPKK peptide in the presence of AQ, which shows that AQ does not block the proteolytic activity of LF at 100 μM.

Figure 11A:
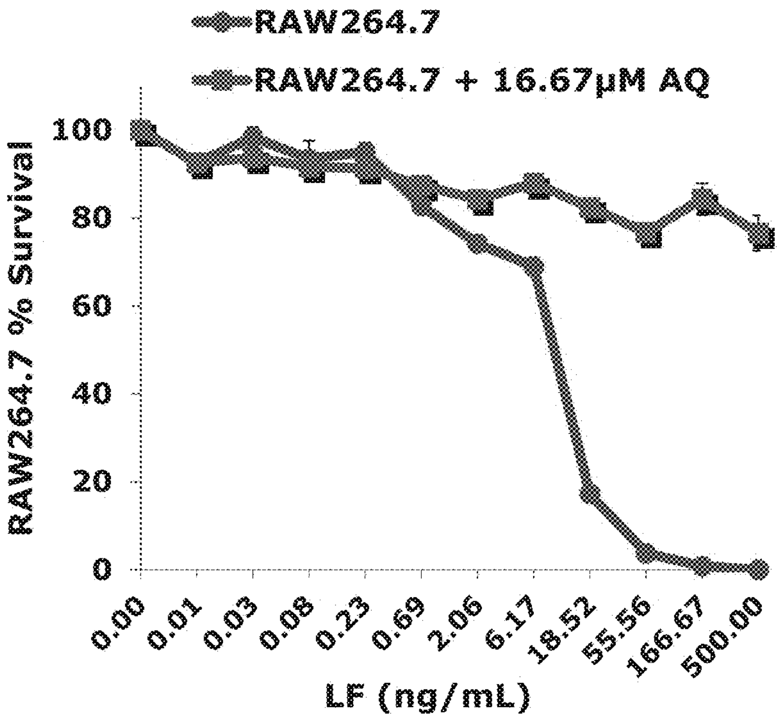
FIG. 11A is a graph showing the percent survival of RAW264.7 cells relative to 500 ng/mL PA with increasing amounts of LF toxin (ng/mL) with 16.67 uM Amodiaquine (AQ) (blue squares) or without (red circles), according to embodiments of the present invention.
Figure 11B:
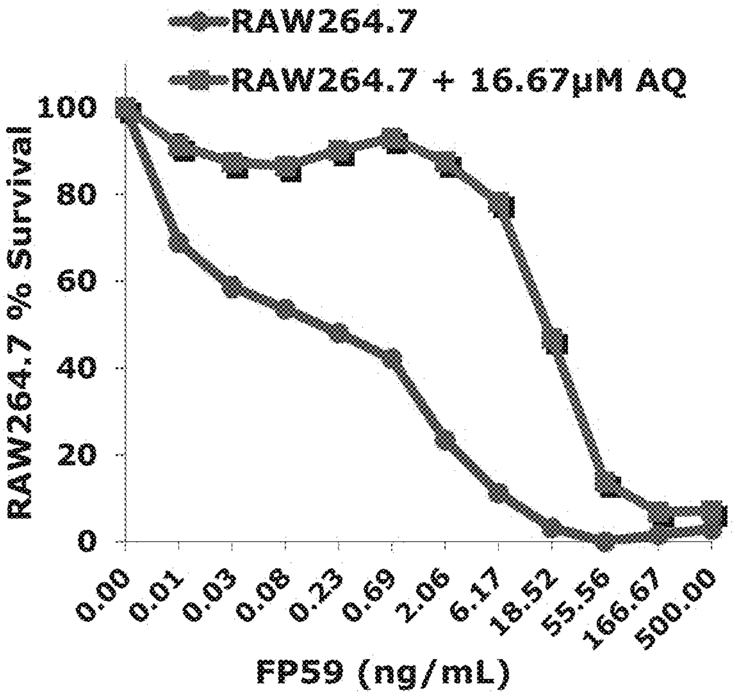
FIG. 11B is a graph showing the percent survival of RAW264.7 cells relative to 500 ng/mL PA with increasing amounts of FP59 toxin (ng/mL) with 16.67 uM Amodiaquine (AQ) (blue squares) or without (red circles), according to embodiments of the present invention.

AQ-treated cells were found to be less sensitive to treatment with PA+FP59 (FIGS. 11A-11B). FP59 is a hybrid toxin, which contains the PA binding site of LF as well as a toxin domain derived from *P. aeruginosa* exotoxin A, that has been widely used as an LF surrogate, and kills cells by a different mechanism. This result, along with the caspase-1 and MEK2 data, strongly suggest that AQ interferes with PA mediated toxin entry.

Example 4

Figure 12:
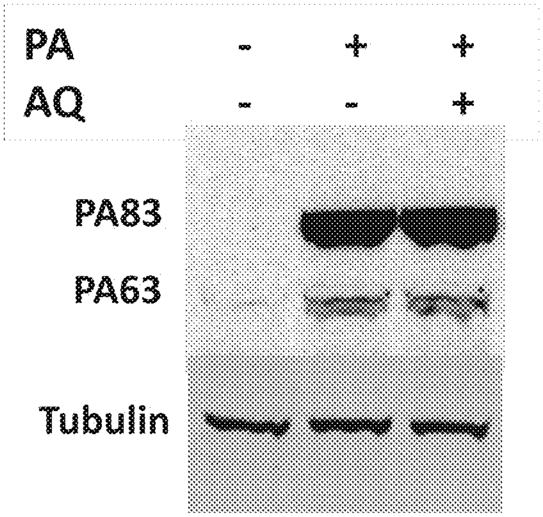
FIG. 12 is an image of a Western immunoblot of cell lysates from RAW264.7 cells incubated with (+) Amodiaquine (AQ) or without (−), for 1 hour prior to addition of 1 ug/mL PA (+) or control (−) for an additional 1 hour as indicated, after which cells were lysed and immunoblotted with PA-specific antibody with tubulin as a loading control, according to embodiments of the present invention.
Figure 13:
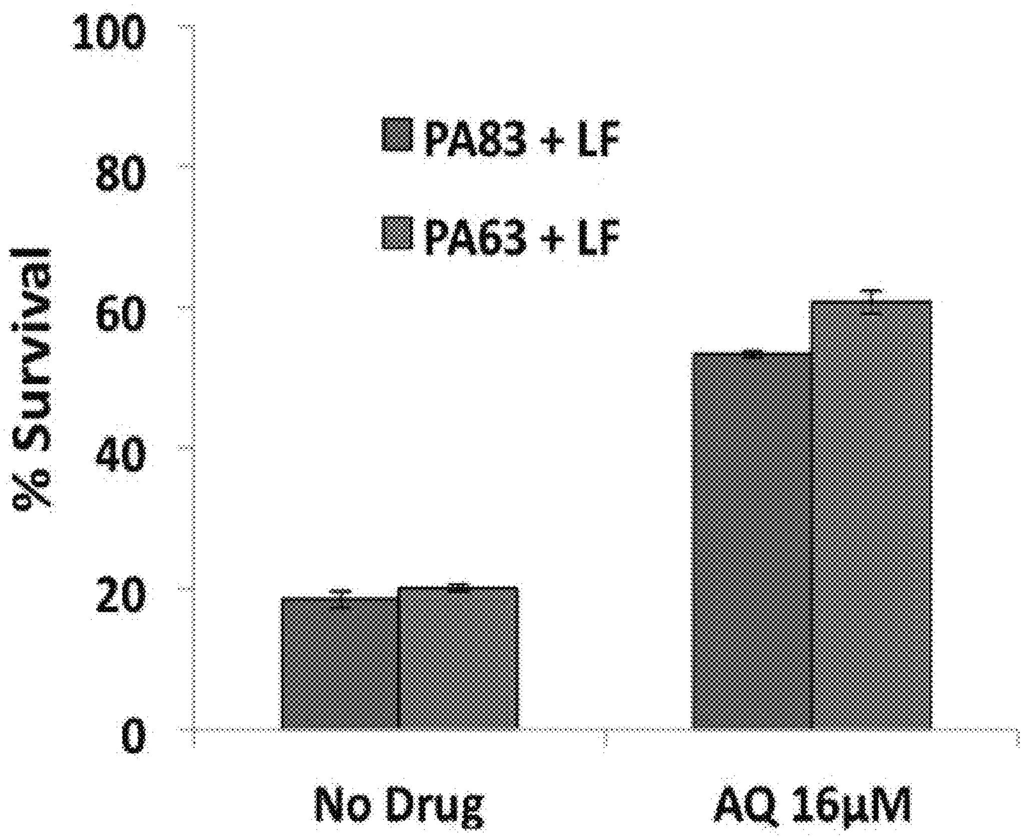
FIG. 13 is a graph showing the percent survival of RAW264.7 cells there were either pretreated with DMSO (No Drug) or with Amodiaquine (AQ) for 1 hour, followed by incubation with 500 ng/mL of LF in the presence of 1.5 ug/ml of either PA83 (blue bars) or PA63 (red bars) for 6 hours, according to embodiments of the present invention.

Amodiaquine binds to and inhibits host cathepsin B. In order for LF to reach the cytosol, PA83 must bind to host cell receptors, be cleaved by furin into PA63, heptamerize into a pre-pore form, bind LF, and proceed to low-pH endosomes where PA-heptamers undergo an acid-dependent conformational change from pre-pore to pore. Host-cell binding of PA and its proteolytic cleavage were monitored by immunoblot in the presence and in the absence of AQ. It was observed that AQ did not block binding of PA83 to cells or block proteolytic processing of PA to generate PA63 (FIG. 12). The inability of AQ to block the activity of host furin cleavage of PA83 is consistent with our observation that AQ equally reduces sensitivity of host cells to both PA83+LF and PA63+LF treatments (FIG. 13). These results indicate that AQ blocks intoxication at a step downstream of PA binding and assembly on the host-cell surface.

Figure 14:
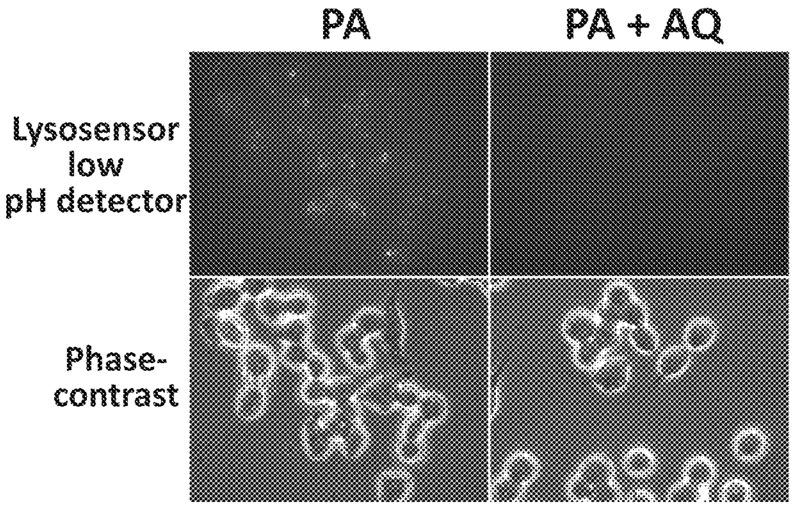
FIG. 14 shows fluorescent microscopic images of RAQ264.7 cells pretreated with Amodiaquine (AQ) or vehicle control for 1 hour, and then treated with 500 ng/mL of PA for an additional hour at 37° C. followed by incubation with the acidic green fluorescent marker, Lysosensor Green DND-189, for 10 minutes, in which PA alone shows increase acidity with green punctate staining, and PA+AQ abolishes the punctate staining as shown, according to embodiments of the present invention.
Figure 15:
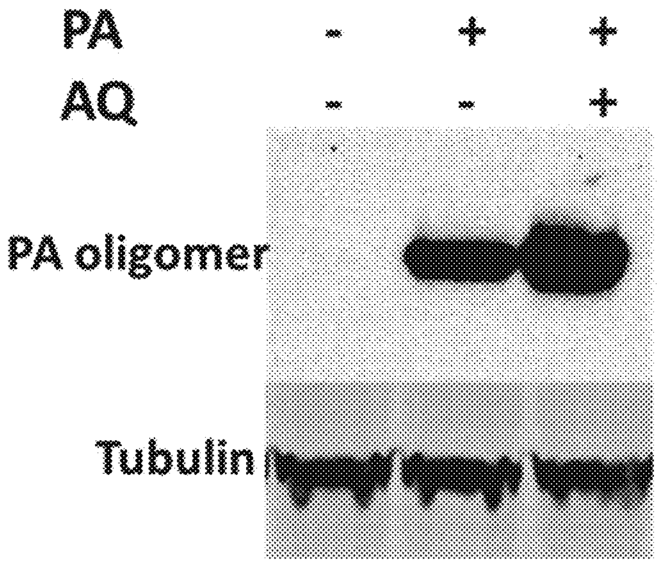
FIG. 15 is an image of a Western immunoblot of cell lysates from RAW264.7 cells pretreated with (+) Amodiaquine (AQ) or without (−) for 1 hour at 37° C., followed by incubation with 1 ug/mL PA at 37° C. for 1 hour, followed by lysis and immunoblotting with a PA-specific antibody with tubulin as a loading control, according to embodiments of the present invention.

CQ was previously shown to prevent endosomal acidification. Since AQ is structurally similar to CQ, it was tested whether AQ neutralizes anthrax toxin induced endosomal acidification. Lysosensor Green DND-189 was used to probe acidic organelles in the cells. Lysosensor is a green fluorescent dye used for tracking acidic organelles in the cell. Neutralization of these compartments is visualized as a loss in punctate-fluorescent structures. In the absence of AQ, PA-treated cells displayed Lysosensor fluorescence, and AQ markedly decreased cell-associated Lysosensor fluorescence (FIG. 14). These results predict that AQ may block the ability of PA to either access acidified endosomes or to form PA pores. It is known that the pore formation of PA, which results from exposure to acidic pH within endosomes, is resistant to dissociation by SDS and runs as an oligomer on SDS-PAGE. Surprisingly, treatment of cells with AQ resulted in higher, rather than lower, abundance of SDS-resistant PA-oligomers compared to cells treated with PA only (FIG. 15).

Figure 16:
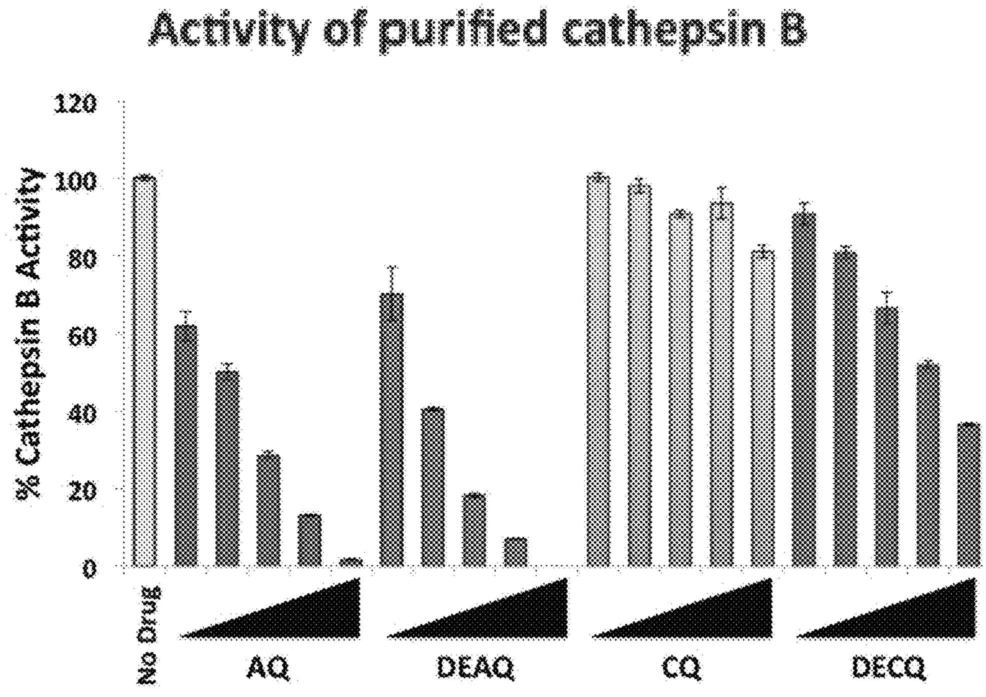
FIG. 16 is a graph showing the percent cathepsin B activity of purified human cathepsin B using a FRET assay to quantify the activity of cathepsin B in the absence of any drug (No Drug, grey bar) or presence of 4, 8, 16, 33, or 66 uM Amodiaquine (AQ) (green bars), N-Desethyl Amodiaquine (DEAQ) (brown bars), Chloroquine (CQ) (blue bars), or Desethyl Chloroquine (DECQ)(red bars), as indicated, according to embodiments of the present invention.
Figure 17:
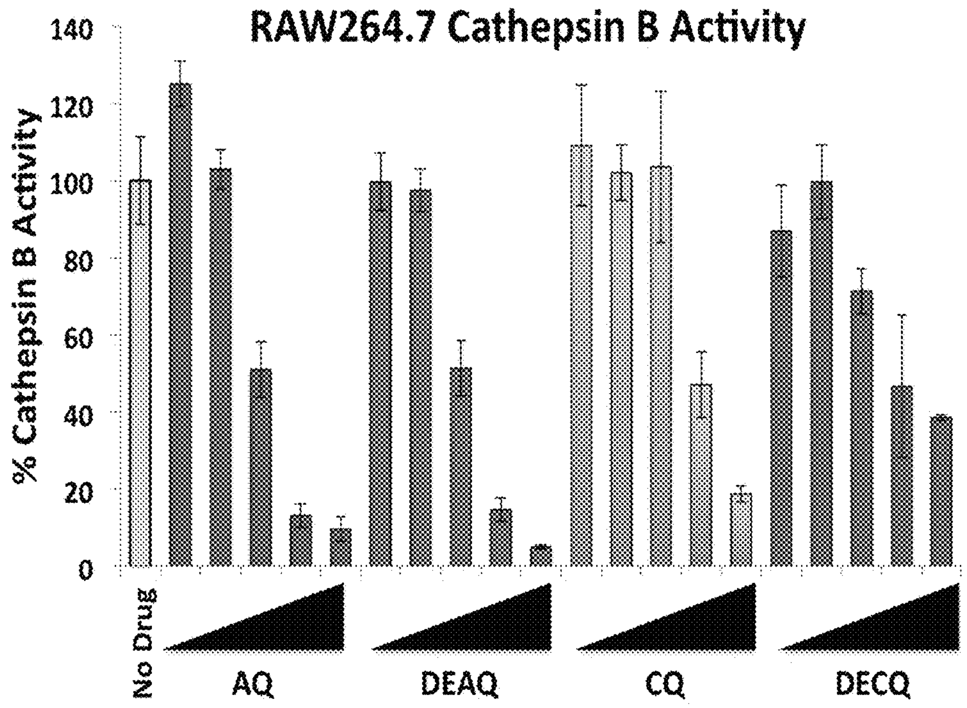
FIG. 17 is a graph showing the percent cathepsin B activity in RAW264.7 cells as measured using a FRET assay to quantify the activity of cathepsin B in the absence of any drug (No Drug, grey bar) or presence of 4, 8, 16, 33, or 66 uM Amodiaquine (AQ) (green bars), N-Desethyl Amodiaquine (DEAQ) (brown bars), Chloroquine (CQ) (blue bars), or Desethyl Chloroquine (DECQ)(red bars), as indicated, for 1 hour prior to cell lysis, followed by FRET analysis, according to embodiments of the present invention.
Figure 18:
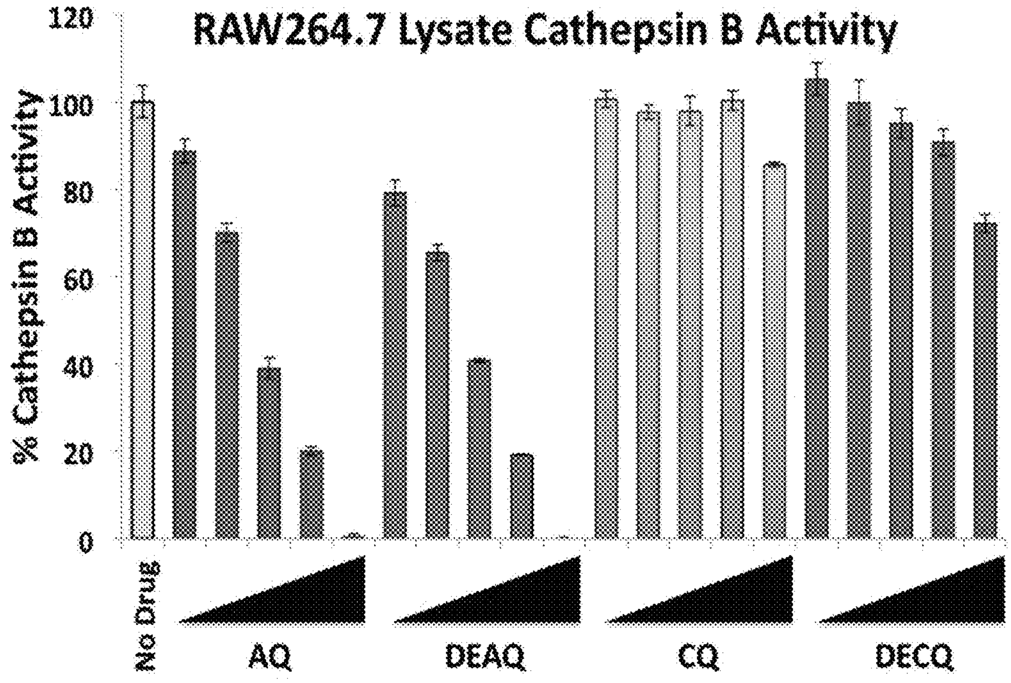
FIG. 18 is a graph showing the percent cathepsin B activity in RAW264.7 cells as measured using a FRET assay to quantify the activity of cathepsin B, in which cells were lysed and cell lysates were incubated in the absence of any drug (No Drug, grey bar) or presence of 4, 8, 16, 33, or 66 uM Amodiaquine (AQ) (green bars), N-Desethyl Amodiaquine (DEAQ) (brown bars), Chloroquine (CQ) (blue bars), or Desethyl Chloroquine (DECQ)(red bars), as indicated, followed by FRET analysis, according to embodiments of the present invention.

A similar observation was previously reported that also showed that an inhibition of host lysosomal cathepsin B by an unrelated small molecule CA-074, resulted in (i) elevated accumulation of PA pores in late endosomes, (ii) the inability of LF to be released from the late endosomes into the cytoplasm, and (iii) results in reduction of cellular sensitivity to LF-PA. Ha et al., 2010, JBC, 285: 2120-2129, the entire content of which is herein incorporated by reference. Upon formation of the SDS-resistant PA63 pore in acidic endosomes, PA pores are then transported to lysosomes for rapid degradation. Ha et al. showed that cathepsin B mediates the fusion of lysosomes with endosomes, and that this fusion is necessary for the release of LF from the endosomes into the cytoplasm. In order to gain further insight into the mechanism of AQ-mediated protection of cells against anthrax toxin killing, it was tested whether AQ inhibits cathepsin B protease activity of purified human cathepsin B using a FRET assay. It was observed that both AQ and DEAQ directly inhibit cathepsin B activity in a dose dependent manner without drug pre-incubation, at drug concentrations used in cellular experiments (FIG. 16). It was tested whether AQ inhibits cathepsin B in RAW264.7 cells. It was observed that cells pre-treated with AQ or with DEAQ for 1hour lost cathepsin B enzymatic activity in a dose dependent manner (FIG. 17). In addition, the ability of AQ to inhibit cathepsin B activity was tested in a protein lysate from cells that were not exposed to drugs prior to the lysis, and it was observed that AQ and DEAQ inhibited cathepsin B activity (FIG. 18). It was determined that the addition of drugs to cathepsin B reactions did not change the pH (pH 5.8) of the reaction buffer. In all of the cathepsin B experiments it was observed that CQ and its metabolite, Desethyl-Chloroquine (DECQ), were weaker inhibitors of cathepsin B activity (FIGS. 16-18), which corresponds to the phenotypic data seen in FIGS. 4A, 4B, 6, and 7.

Figure 19A:
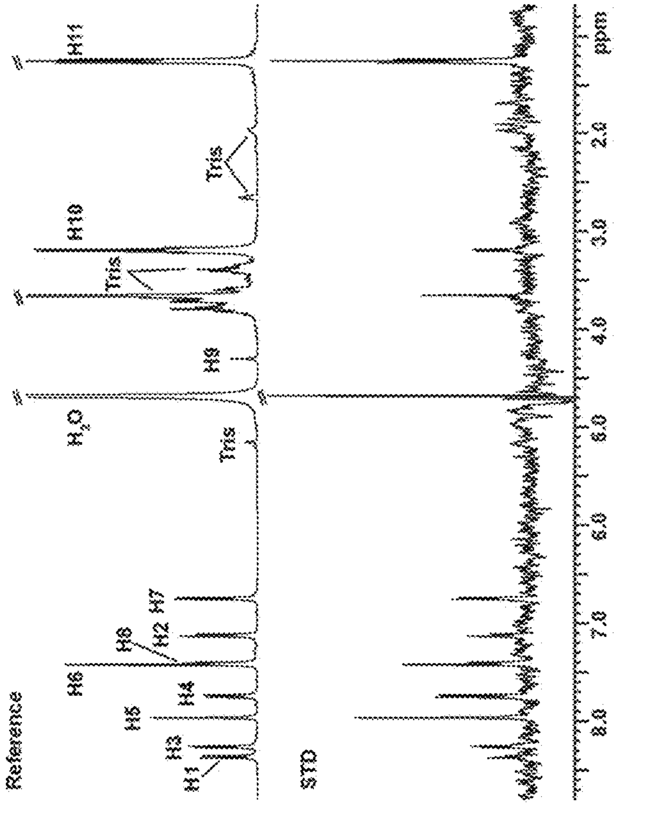
FIG. 19A is H-NMR spectra of AQ in the presence of cathepsin B with the reference spectrum of AQ with its atoms labeled (top spectrum) and the saturation transfer difference (STD) spectrum shown on the bottom, according to embodiments of the present invention.
Figure 19B:
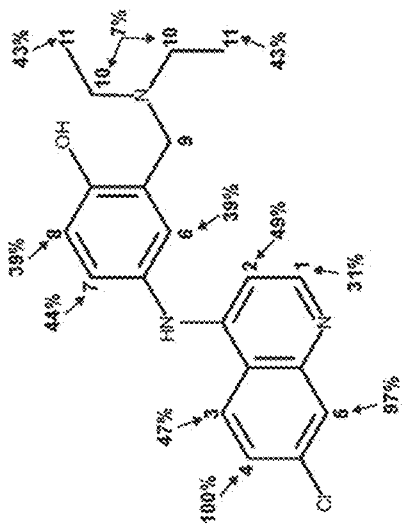
FIG. 19B shows the chemical structure of Amodiaquine (AQ) showing the atom-specific magnitude of the STD effects, in which the STD effect was calculated according to the formula $A_{STD}=(I_0-I_{sat})/I_0$, and all STD effects are expressed as a percentage relative to the H4 atom (100%), according to embodiments of the present invention.

The interaction between AQ and cathepsin B was probed using saturation transfer difference NMR spectroscopy (STD). This technique is a powerful label-free ligand-observed tool to study molecular interactions in solution. STD relies on the transfer of selective saturation (excitation) of the protein's atoms to atoms located in the bound ligand. Two 1D $^1$H-NMR spectra are acquired—one in which the protein's signals are selectively saturated ("on" resonance, $I_{sat}$), and another in which no signals are saturated ("off" resonance, $I_0$). Ligand binding is evident by the difference spectrum ($I_0$-$I_{sat}$), as only when binding occurs are the signals of the ligand affected. FIG. 19A shows the $^1$H-NMR spectrum of 2 mM AQ in the presence of 20 μM cathepsin B (ligand:protein molar ratio of 100:1), and its corresponding STD difference spectrum. The presence of AQ signals in the difference spectrum clearly indicates that it is binding to the enzyme. An inspection of the atom-specific effects provides insight into the mode of binding. Atoms in the quinoline backbone display the largest reduction in their intensities, suggesting that they are in close proximity to cathepsin B (FIG. 19B, atoms H4 and H5 exhibit STD effects of 100 and 97%, respectively). In contrast, the H9 and H10 methylene protons are modestly affected suggesting that in the complex they are located distal to hydrogen atoms in the protein. Interestingly, several atoms in the phenol ring display substantial STD effects suggesting that they are near the protein. This is consistent with the lower biological activities of AQ analogs that remove the phenol ring (FIGS. 4A, 4B, 5A, 5B, 5C, 6, and 7). The importance of the AQ quinoline ring revealed by STD is also compatible with the crystal structure of cathepsin B bound to nitroxoline, as this small molecule contains a quinoline moiety that interacts extensively with the enzyme.

Example 5

Amodiaquine inhibits pathogenicity of Ebola virus. Upon observing that AQ protects cells from anthrax and diphtheria toxins, it was hypothesized that AQ and DEAQ might also be able to inhibit the entry of Ebola virus. Ebola virus, among other viruses, requires low endosomal pH, as well as host cathepsin B function for membrane fusion and infection of host cells. In fact, AQ and CQ have been reported to inhibit Ebola virus pathogenicity in cells. (Gnirss et al., 2012, *Virology,* 424:3-10 and Sanchez, 2007, *J. Infect. Dis.* 196 Suppl 2:S251-258, the entire contents of both of which are incorporated herein by reference. The ability of AQ and CQ to inhibit Ebola virus abundance in infected HeLa cells was re-tested by visualizing infected cells using immune-staining, including the ability of their metabolites, DEAQ and DECQ, to inhibit Ebola virus propagation in cultured cells in vitro. To test AQ-mediated inhibition of viral propagation, infection by Ebola virus (Kikwit) at MOI of 0.5 was compared with and without drugs for 48 hours. In order to detect infected cells, immuno-staining was completed with anti-Ebola-glycoprotein antibodies. AQ and DEAQ effectively inhibited propagation of Ebola virus in HeLa cells with EC50's in the low μM range (Table 1): the EC50's of AQ and DEAQ were 3.8 and 3.6 μM respectively. The EC50's of CQ and DECQ in HeLa were 4.8 and 7.3 μM respectively. This data shows that DEAQ is more efficacious in inhibiting Ebola propagation compared to DECQ.

TABLE 1

| HeLa cells | | | | | |
|---|---|---|---|---|---|
| Pathogen | Drug, hours | EC50 μM | SD μM | CC50 μM | SI50 |
| EBOV | AQ, 48 h | 3.8 | 0.38 | 50 | 13.2 |
| EBOV | DEAQ, 48 h | 3.6 | 0.35 | 50 | 13.9 |
| EBOV | CQ, 48 h | 4.8 | 0.57 | 100 | 20.7 |
| EBOV | DECQ, 48 h | 7.3 | 0.55 | 100 | 13.8 |

Similar results were obtained by testing AQ, CQ, DEAQ, and DECQ for their ability to inhibit Ebola virus in the primary human cell line, HFF-1 (Table 2). This result confirms that anti-viral effect of AQ is not related to its effects on the host cell cycle or cellular proliferation.

TABLE 2

| HFF-1 cells | | | | | |
|---|---|---|---|---|---|
| Pathogen | Drug, hours | EC50 μM | SD μM | CC50 μM | SI50 |
| EBOV | AQ, 48 h | 2.6 | 0.19 | 30 | 11.4 |
| EBOV | DEAQ, 48 h | 2.1 | 0.48 | 30 | 14.4 |
| EBOV | CQ, 48 h | 2.5 | 0.88 | 70 | 28.0 |
| EBOV | DECQ, 48 h | 3.2 | 0.62 | 70 | 22.1 |

The life cycle of Ebola virus in cultured host cells is 20-24 hours. In order to more clearly evaluate effects of AQ and DEAQ on a single viral life cycle, the inhibitory effects of these drugs were compared after 24 and 48 hours (h) of Ebola virus infection in cells. It was observed that AQ and DEAQ are at least two times more potent after 24 h of infection (EC50's 2 μM), compared to 48 h, during which time the secondary round of infection occurs and possibly slightly decreases the antiviral efficacies of AQ and DEAQ (EC50's 4 μM) (Table 3). Table 3 shows the effect of time of AQ and DEAQ on the pathogenicity of EBOV in which the 50% effective (EC50, virus inhibitory) concentrations and 50% cytotoxic (CC50, cell inhibitory) concentrations are shown, and CC50 divided by EC50 indicates the selectivity index (SI) value.

TABLE 3

| Pathogen | Drug, hours | EC50 μM | SD μM | CC50 μM | SI50 |
|---|---|---|---|---|---|
| EBOV | AQ, 24 h | 2.38 | 0.47 | >50 | >21 |
| EBOV | AQ, 48 h | 4.46 | 0.44 | >50 | >11.2 |
| EBOV | DEAQ, 24 h | 2.15 | 0.48 | >50 | >23.3 |
| EBOV | DEAQ, 48 h | 4.12 | 036 | >50 | >12.1 |

Example 6

Amodiaquine inhibits pathogenicity of other Category A, B, and C pathogenic agents that enter into host cytoplasm from acidified endosomes. In addition to anthrax toxin, diphtheria toxin, and Ebola virus, other pathogenic agents SARS coronavirus, Venezuelan equine encephalitis virus (VEEV), Rabies virus, Junin virus, Chikungunya virus, and *Clostridium difficile* toxin B enter the cytoplasm from endosomes and all require the acidification of endosomes. It was demonstrated that all of those pathogenic agents are inhibited by AQ in their respective in vitro cellular assays (*Material and Methods, Table* 4, FIG. 6C). Table 4 shows the ability of drugs to reduce the abundance of the indicated pathogens viruses (EC50) or cytotoxicity (CC50) induced by bacteria toxins in host cells in which the cells were analyzed described for Table 1 above.

TABLE 4

| Pathogen | EC50 μM | CC50 μM | SI50 |
|---|---|---|---|
| Pathogen known to enter into cytoplasm from Endosomes low pH-dependent | | | |
| Ebola Virus | 2.4 | >50 | >20 |
| SARS coronavirus | 2.4 | 32 | 13.3 |
| Venezuelan equine encephalitis virus | 3.2 | 31 | 9.7 |
| Rabies | 5.7 | >10 | >2 |
| Junin | 16.9 | 50 | 3.0 |
| Chikungunya | 18.3 | >50 | >2 |
| *Clostridium difficile* Toxin B | 4.6 | 30.7 | 6.7 |
| Entry into cytoplasm from Endoplasmic Reticulum | | | |
| Poliovirus 3 | >100 | >100 | 1 |
| Herpes simplex virus 1 | >60 | >60 | 1 |
| Cholera Toxin | >66.7 | >66.7 | 1 |
| *Pseudomonas aeruginosa* Exotoxin A | >66.7 | >66.7 | 1 |
| Pathogens known to enter into cytoplasm, low PH-independent | | | |
| Human Cytomegalovirus | >60 | >60 | 1 |
| Respiratory syncytial virus | 32 | 32 | 1 |

The ability of DEAQ to inhibit pathogenicity of Junin virus (JUNV) and Chikungunya virus (CHIV) was also tested, and it was observed that DEAQ inhibits those two viruses with EC50's similar to those of AQ (Table 5). The effect of AQ and DEAQ on the pathogenicity of CHIV and JUNV was measured in HFF-1 cells. The ability of drugs to reduce the abundance of viruses in host cells was measured in cells by fluorescent microscopy.

TABLE 5

| Pathogen | Drug | EC50 μM | SD μM | CC50 μM | SI50 |
|---|---|---|---|---|---|
| CHIV | AQ | 18.4 | 0.56 | >50 | >2 |
| CHIV | DEAQ | 17.3 | 0.64 | >50 | >2.9 |
| JUNV | AQ | 16.9 | 1.92 | 50 | 3.0 |
| JUNV | DEAQ | 13.8 | 2.02 | 40 | 2.9 |

Other pathogenic agents, including cholera toxin, *Pseudomonas aeruginosa* exotoxin A, Poliovirus 3, and Herpes simplex virus 1 are transported in a retrograde fashion to the endoplasmic reticulum (ER) and retrotranslocated into the cytoplasm by the host ER-associated degradation pathway. It was observed that cytotoxicity mediated by those pathogens was not blocked by AQ (Table 4 and FIGS. 20A, 20B). In addition, the inability of AQ to inhibit cholera and *Pseudomonas* toxins, which are both ADPrybosyltransferases, suggests that AQ's adverse effect on diphtheria toxin (FIGS. 2 and 6B.), which is also ADP-rybosyltransferase, occurs by inhibition of host cathepsin B only.

Another group of pathogens enter the cytoplasm by ways that do not rely on the acidification of endosomes, and include Human Cytomegalovirus and Respiratory syncytial virus. It was determined that AQ did not reduce the pathogenicity of those viruses (Table 4). This data supports the conclusion that AQ inhibits the entry of toxins into the cytoplasm from acidified endosomes.

Example 7

Materials and Methods

Chemicals and Reagents. All toxins were purchased from List Biological Laboratories. FP59 was a kind gift from S. Leppla (National Institute of Allergy and Infectious Diseases/National Institutes of Health, Bethesda, Md.). An FDA-approved drug library comprising of 1,581 drugs was purchased from Johns Hopkins, titled, Johns Hopkins Clinical Compound Library (JHCCL) version 1.0. The drugs arrived as 10 mM stock solutions in sealed microtiter plates and were made using DMSO or water as solvents. Drugs were arrayed in 96-well plates and screened at a stock concentration of 3.3 mM. Amodiaquine, Chloroquine, Cinchonine, Primaquine, and Quinidine were purchased from Sigma-Aldrich (St. Louis, Mo., USA). All drugs were prepared at 10 mM using DMSO as a solvent. N-Desethyl Amodiaquine and desethyl-chloroquine were purchased from Toronto Research Chemicals Inc. Anti-N-terminal MEK-2, anti-tubulin, and anti-PA antibodies were purchased from Santa Cruz Biotechnology. Purified human cathepsin B protein used for NMR experiments was purchased from ACROBiosystems.

Cellular Drug Screens. RAW264.7-pGIPZ(−)mouse macrophage cells were maintained in DMEM (Sigma-Aldrich) supplemented with 10% FBS (Bioexpress) and 100 μg/mL penicillin and 100 μg/mL streptomycin. RAW264.7-pGIPZ (−) cells (10,000 per well) were seeded in 96-well plates (100 μl/well) 24 hours before the assay. During the drug library screen assay, 0.75 μl of 3.3 mM drugs were added to 150 μl of cell-containing media to achieve 16 μM of each compound per well. Cells were treated with compounds for 1 hour at 37° C. 5% $CO_2$, and then challenged with anthrax toxins, such that the final toxins concentrations were 0.5 μg/ml. Cells were treated with toxin and drugs for 6 hours. As rodent cells are resistant to diphtheria toxin, C32 human melanoma cell line was used for diphtheria toxin screening, where cells were treated with 2 μg/ml for 24 hours. Determination of cell viability by 3-(4,5-dimethylthiazol-2-yl)-2, 5-diphenyltetrazolium bromide (MTT) assay was performed as described in Lu et al., 2004, *PNAS,* 101:17246-17251, the entire content of which is incorporate herein by reference. Cell viability is shown as the percentage of surviving cells obtained relative to cells treated with DMSO (100%).

FRET MAPKKide LF activity. For drug testing in 96-well plates, the reaction volume was 250 μl per well, containing 20 mM HEPES pH 7.2, 5 μM MAPKKide conjugated with DABCYL and FITC (List Biological Laboratories, Inc), and 100 μM of JHCCL compound. The reaction was initiated by adding LF to a final concentration of 5.8 μg/ml. Kinetic measurements were obtained at 37° C. every 40 seconds for 40 minutes using a fluorescent plate reader. Excitation and emission wavelengths were 490 nm and 523 nm, respectively, with a cutoff wavelength of 495 nm.

Toxins Treatments. Cells were seeded in a 96-well plate at a density of 10,000 cells/well 1 d before toxin treatment. Various concentrations of LF or FP59 combined with a fixed concentration of PA (500 ng/mL) were added to the wells, and cells were incubated for 6 h at 37° C. Cell viability was measured by MTT assay. In other toxin treatment experiments, cells were pre-treated with various concentrations of drugs, and then treated with constant concentrations of 8.3 µg/ml of *C. difficile* toxin B, 500 ng/ml of *P. aeruginosa* Exotoxin A, or 500 ng/ml of Cholera toxin for 6 hours. RAW264.7 cell survival was measured by MTT assay. Each data point shown for MTT assays indicates the mean±SD value obtained in triplicate assays done in a representative experiment. At least three such experiments were routinely carried out.

MEK Cleavage Assay. RAW264.7 cells were pre-treated with 66.67 µM of AQ for 1 hour. Following the pre-treatment, the cells exposed to 1 µg/mL of PA and LF at 37° C. for up to two hours in the presence of 16.67 µM of AQ. The cells were then washed with cold PBS for 5× and lysed with RIPA buffer containing a protease inhibitor mixture (Roche). Cell lysates were quantified using the BCA protein quantification kit (Pierce) and loaded onto 4-12% denaturing gels (Criterion XT Precast Gel, Bio-Rad). After electrophoresis for several hours, the gel was transferred overnight to nitrocellulose membranes; membranes were probed with anti-MEK-2 or anti tubulin antibodies. Quantitative Western blot analyses of the bands were accomplished using the VersaDoc 1000 instrument (Bio-Rad) or Odyssey infrared imaging system (LI-COR Biosciences).

Biochemical Assay of PA Binding and Internalization. Cells were pre-treated with AQ as described above for lh, either at 4° C. for PA binding or at 37° C. for PA internalization assays cells were exposed to 1 µg/mL of PA at 4° C. for 1 h for binding assay or at 37° C. for 1 h for internalization assay. Cells were then washed with PBS solution three times and lysed in Radioimmunoprecipitation assay (RIPA) buffer containing a protease inhibitor mixture (Roche). Western blot analysis was performed using anti-PA antibody anti-tubulin monoclonal antibody (Sigma-Aldrich). Chemiluminescence of bands and their relative intensities were revealed using a VersaDoc 1000 instrument (Bio-Rad).

Caspase-1 Activity Assay. Cells were treated with AQ for 1 h before addition of 500 ng/ml LF-PA for an additional 2 h. FAM FLICA™ Caspase 1 Assay Kit was obtained from ImmunoChemistry Technologies LLC. FLICA reagent was added for 1 h. FLICA fluorescence was visualized as follows: cells were washed three times in PBS, fixed in 4% (wt/vol) paraformaldehyde, and examined under a fluorescence microscope (DM5500 B; Leica).

Staining Cells with Lysosensor Green DND-189. Cells were treated with AQ for 1 hour before an addition of 500 ng/ml PA for an additional hour and then stained with Lysosensor Green DND-189 for 10 min at 37° C. Cells were then washed and fluorescence was visualized as follows: cells were fixed in 4% (wt/vol) paraformaldehyde, and examined under a fluorescence microscope (DM5500 B; Leica).

Cathepsin B Activity Assay. Cathepsin B activity in total cell lysates was determined using an InnoZyme™ cathepsin B activity assay kit (EMD Milipore) and performed according to the manufacturer's instruction. Cathepsin B activity in cellular lysates was tested as follows: RAW264.7 cells untreated with drugs were lysed, and equal amount of cathepsin B containing protein lysate was added to the substrate solution (EMD Millipore) with and without AQ, CQ, DEAQ, or DECQ at concentrations of 4, 8, 16, 33, or 66 µM. Cellular cathepsin B activity with and without drugs was tested by pre-treating cells with drugs for 1 hour, followed by lysing cells and testing cathepsin B activity with a fluorescently labeled substrate. The activity of 0.5 ng/µl of purified human cathepsin B was mixed with and without drugs without pre-incubation and detected with a fluorescently labeled substrate. Fluorescence intensity indicating cathepsin B activity was measured at an excitation wavelength of 370 nm and emission wavelength of 450 nm (Molecular Devices, Spectra Max 384 PLUS).

Rat intoxication challenge. The rat studies were performed at Explora Biolabs, San Diego, Calif. following Institutional Animal Care and Use Committee (IACUC) approved protocols. Five Male Sprague-Dawley rats (226 to 250 g; Charles River) per group were used. The toxin mixture was prepared for each group by mixing 12 µg of LF with 40 µg of PA or with 1.5, 3.0, or 6.0 mg/kg of Amodiaquine in a 500 µl volume per rat. Rats were monitored for signs of clinical illness or death for 14 days after the challenge.

NMR spectroscopy. All STD experiments were performed at 25° C. using a Bruker Avance 500-MHz spectrometer equipped with a cryogenic probe. The pulse scheme employed excitation sculpting with gradients, and a 50 ms spin lock filter ($T_{1p}$) to suppress signals originating from the water and protein signals, respectively. An irradiation power of 26 Hz was applied on-resonance at 0.04 ppm, and off-resonance at 30 ppm, for a total saturation time of 4 s. Spectra were collected in an interleaved manner to account for any temporal fluctuations. Separate control experiments were performed using samples of cathepsin B or Amodiaquine to confirm the selectivity of saturation. STD spectra were acquired with 4096 scans and 32 k data points using a spectral width of 7002.8 Hz centered at 2352 Hz. All experiments were performed in deuterated tris buffer: 50 mM $D_{11}$-Tris, 150 mM NaCl, pH 7.5 supplemented with 8% $D_2O$. The sample used for STD measurements contained 20 mM and 2 mM cathepsin B and Amodiaquine, respectively. The STD NMR data were processed and analyzed using Topspin 3.1 software (Bruker, Billerica Mass.). STD effects were calculated according to the formula: $A_{STD}=(I_0-I_{sat})/I_0$, where $I_{sat}$ and $I_0$ are the intensity of the Amodiaquine signal recorded with and without saturation of the protein, respectively.

Viral tests. Specifically, infection of HeLa cells with Ebola was done using Ebola virus (Kikwit) MOI=0.5 (calculated for 4,000 cells/well, assuming one complete round of replication of HeLa cells at 15±2 hrs after cell seeding). Cells were incubated with the virus for 24 or 48 h. Infection was terminated by fixing samples in formalin solution, and immuno-staining was used to visualize infected cells. Cells were treated with anti-GP specific monoclonal antibody (6D8) (1 to 1000 dilution) followed by anti-mouse IgG conjugated with Dylight488 (Thermo) (1 to 1000 dilution) in blocking buffer containing 3% BSA in PBS. Nuclei were stained with Draq5(Biostatus) diluted in PBS buffer. Images were acquired on the Opera imaging instrument (Perkin Elmer) using 10× Air objective and four images/well were acquired and analyzed using PE Acapella algorithms.

Screening Assays for Ebola Virus (EBOV, Strain Kikwit).

High Content Imaging virus infection assay. Cell Culture and infection: HeLa cells (ATCC) were cultured for 3 days in T175 or T225 (Corning) flasks in culture media containing Minimum Essential Medium (MEM, Corning Cellgro) supplemented with 10% Fetal Bovine Serum (Hyclone), 1% L-Glutammine (Hyclone), 10 mM Hepes 7.0-7.6 (Sigma), 1% non-essential amino acids (Sigma). Cells were lifted using Trypsin-EDTA (Sigma, T3974) and 2,000 cells/well were plated in 35 μl of culture media into imaging 384 well assay plates (Aurora 384, IQ-EB, 384 IQ-EB/NB, 200 mclear, #1052-11130) and incubated for about 20 h before compound treatment.

Compound treatment. Treatment of the cells with test and control compounds was done 2 h prior infection. EC50 determination for test compound done with 2 fold step at least for 10 doses starting from highest concentration of 100 uM (with stock concentration of 10 mM) using HP D-300 digital dispenser. Each dose dispensed directly from the concentrated stock with highest volume of 500 nL. Concentration of DMSO in all wells was normalized to 1%. Cells were pre-treated with serially diluted compounds for 2 hours before infection. Each dose was repeated 4 times on one plate (n=4).

Infection. Infection was done using Ebola virus (Kikwit) MOI=0.5 (calculated for 4,000 cells/well, assuming one complete round of replication of HeLa cells at 15±2 hrs after cell seeding) and 10 ul of virus dilution was dispensed in each well except column 2, representing "no infection control". Cells were incubated with the virus for 24 or 48 h. Infection was terminated by fixing samples in formalin solution.

Immuno-staining assay. Immune-staining was used to visualize infected cells. Cells were treated with anti-GP specific monoclonal antibody (6D8) (1 to 1000 dilution) followed by anti-mouse IgG conjugated with Dylight488 (Thermo) (1 to 1000 dilution) in blocking buffer containing 3% BSA in PBS. Nuclei were stained with Draq5 (Biostatus) diluted in PBS buffer.

Image and Data analysis. Images were acquired on the Opera imaging instrument (Perkin Elmer) using 10× Air objective and four images/well were acquired. Signal from anti-virus staining was detected at 488 nm emission wavelength and Nuclei at 640 nm. Image analysis was performed using PE Acapella algorithms. Several well-based output parameters were measured including: Number of Objects (Nuclei) and Positive Virus Number of Objects (Ave of Intensity for virus specific signal). The % of Infected cells was calculated by Acapella directly as $$\%\ \text{Infected cells} = \frac{\text{Positive Virus Number of Objects }(s)}{\text{Number of objects }(s)} * 100$$

% infection rate was analyzed for each plate using Median of % Positive virus cells (for all Neutral control wells that are infected and treated with DMSO only; S-sample.

Data analysis. Data normalization was done using GeneData Explorer software. Data was normalized on the plate based level converting the % Virus positive cells associated with each wells into % Activity=% of inhibition of infection (or % Inhibition or % INH). Control wells were indicated as follows:

NC=Neutral control; Infection+DMSO (or minimal activity of inhibitor)

BC=Blank control; No infection (or maximum inhibition of viral infection possible). Median of the values is used for all controls.

$$\%\ \text{Inhibition} = \frac{\text{Median \% Virus positive}(NC) - \text{\% Virus positive}(S)}{\text{Median \% Virus positive}(NC) - \text{Median \% Virus positive}(BC)} * 100\%$$

% Percent Viability. The number of objects represented the amount of cells in each treated well and was also used as indication of the cyto-toxic or cyto-static effect. The number of objects was converted by GeneData Condoseo to % Viability for with a compound dose response.

$$\%\ \text{Viability} = \frac{\text{Nuclei Number Sample}}{\mathit{MedianNuclei}\ \text{number }(NC)} * 100\%$$

Dose response curve fitting analysis. Analysis of dose response curve for % Inhibition and % Viability was used to determine $EC_{50}$ and $CC_{50}$, and was applying GeneData Condoseo software with Levenberg-Marquardt algorithm (LMA) for curve fitting strategy. The Curve-fitting applied validity criteria, such aschi$^2$, SE log$EC_{50}$, minimal number of valid data points, to indicate if curve fitting converging was successful and indicated in table with results. $R^2$value quantifies goodness of fit. Fitting strategy was considered acceptable if it gave conversion with $R^2$>0.8.

Screening Assays for Venezuelan equine encephalitis virus (VEEV, Strain TC-83). Primary cytopathic effect (CPE) reduction assay. Four-concentration CPE inhibition assays are performed. Confluent or near-confluent cell culture monolayers in 96-well disposable microplates are prepared. Cells are maintained in MEM or DMEM supplemented with FBS as required for each cell line. For antiviral assays the same medium is used but with FBS reduced to 2% or less and supplemented with 50 μg/ml gentamicin. The test compound is prepared at four $\log_{10}$ final concentrations, usually 0.1, 1.0, 10, and 100 μg/ml or μM. The virus control and cell control wells are on every microplate. In parallel, a known active drug is tested as a positive control drug using the same method as is applied for test compounds. The positive control is tested with each test run. The assay is set up by first removing growth media from the 96-well plates of cells. Then the test compound is applied in 0.1 ml volume to wells at 2× concentration. Virus, normally at <100 50% cell culture infectious doses (CCID50) in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ until maximum CPE is observed in virus control wells. The plates are then stained with 0.011% neutral red for approximately two hours at 37° C. in a 5% $CO_2$ incubator. The neutral red medium is removed by complete aspiration, and the cells may be rinsed 1× with phosphate buffered solution (PBS) to remove residual dye. The PBS is completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well is quantified using a 96-well spectrophotometer at 540 nm wavelength. The dye content in each set of wells is converted to a percentage of dye present in untreated control wells using a Microsoft Excel computer-based spreadsheet. The 50% effective ($EC_{50}$, virus-inhibitory) concentrations and 50% cytotoxic ($CC_{50}$, cell-inhibitory) concentrations are then calculated by linear regression analysis. The quotient of $CC_{50}$ divided by $EC_{50}$ gives the selectivity index (SI) value.

Screening Assays for Herpes Simplex Virus 1 (HSV-1, Strain E-377) and Human Cytomegalovirus (CMV Strain AD169). Human foreskin fibroblast (HFF) cells were prepared from human foreskin tissue. The tissue was incubated at 4° C. for 4 h in Clinical Medium and then placed in phosphate buffered saline (PBS) to remove the red blood cells, and resuspended in trypsin/EDTA solution. The tissue suspension was incubated at 37° C. and gently agitated to disperse the cells, which were collected by centrifugation. Cells were resuspended in 4 ml Clinical Medium and placed in a flask and incubated at 37° C. in a humidified $CO_2$ incubator for 24 h. The media was then replaced with fresh Clinical Medium and the cell growth was monitored daily until a confluent monolayer has formed. The HFF cells were then expanded through serial passages in standard growth medium of MEM with Earl's salts supplemented with 10% FBS and antibiotics. The cells were passaged routinely and used for assays at or below passage 10.

Primary Cytopathic Effect (CPE) Reduction Assay. Low passage (3-10) HFF cells were trypsinized, counted, and seeded into 96 well tissue culture plates in 0.1 ml of MEM supplemented with 10% FBS. The cells were then incubated for 24 h at 37° C. The media was then removed and 100 μl of MEM containing 2% FBS was added to all but the first row. In the first row, 125 μl of media containing the experimental drug was added in triplicate wells. Media alone was added to both cell and virus control wells. The drug in the first row of wells was then diluted serially 1:5 throughout the remaining. The plates were then incubated for 60 min and 100 μl of a virus suspension was added to each well, excluding cell control wells which received 100 μl of MEM. The plates were then incubated at 37° C. in a $CO_2$ incubator for three days for HSV-1, or 14 d for CMV. After the incubation period, media was aspirated and the cells stained with crystal violet in formalin for 4 h. The stain was then removed and the plates were rinsed until all excess stain was removed. The plates were allowed to dry for 24 h and the amount of CPE in each row determined using a BioTek Multiplate Autoreader. $EC_{50}$ and $CC_{50}$ values were determined by comparing drug treated and untreated cells using a computer program.

Screening Assays for Rabies (Strain Flury). Confluent BHK-21 cells were prepared in T-150 flask. Cells were Trypsinized cells and made as cell suspensions. 50 μl of $5\times10^5$ cells/ml cell suspension (25,000 cells/well) were added into each well of the 96 well plates, except row H. 2× concentration of antivirals were made (Isoprinosine and test drug(s)). 6 concentration points are done. 100 μl per well that will be tested for effective concentration (drug wells) and cytotoxic concentration (tox wells) were added. The rabies virus was diluted 1:1000. 50 μl was added per well in the drug wells and virus control wells. This gave a final dilution of 1:4000. The final volume was 200 μl Additional media was added to fill up wells, i.e.: Tox wells were 100 μl 2× drug, 50 μl cells (5e5 cells/ml), and 50 μl media. Plates were covered and incubated (37° C.; 5% $CO_2$) for 5 days. After 5 days the Promega CellTiter-Glo Luminescent Cell Viability Assay was run using the Fluoroskan FL to scan for luminescence.

Screening Assays for Poliovirus 3.

Principal Viruses and Cells. Poliovirus: WM3, Cells: LLC-MK2 clone 7.1.

CellTiter 96 (Cytopathic effect/Toxicity). The primary screen is a cytopathic effect (CPE) reduction assay. Briefly, 96-well cultures of cells are infected with virus in the presence of test compounds and incubated for 4-7 days (depending on the specific virus/cells). Each virus is pre-titered such that control wells exhibit approximately 95% loss of cell viability due to virus replication. Therefore, antiviral effect, or cytoprotection, is observed when compounds prevent virus replication. Each assay plate contains cell control wells (cells only), virus control wells (cells plus virus), compound toxicity control wells (cells plus compound only), compound colorimetric control wells (compound only, no cells or virus), as well as experimental wells (compound plus cells plus virus). Cytoprotection and compound cytotoxicity are assessed by MTS (CellTiter®96 Reagent, Promega, Madison Wis.) dye reduction. The % reduction in viral CPE (antiviral activity) and % cell viability (cytotoxicity) are determined and reported.

Screening Assays for Respiratory syncytial virus and SARS CoV.

Principal Viruses and Cells: Respiratory syncytial virus (RSV): Strain A-2 in Hep2 cells SARS CoV: Strain Urbani in Vero76 cells.

CellTiter-Glo (Cytopathic effect/Toxicity). The antiviral cytoprotection assays examine the effects of compounds at designated dose-response concentrations in specific cell types to test the efficacy of the compounds in preventing the virus-induced cytopathic effect. Ribavirin is included as a positive control drug for influenza and RSV, while calpain IV inhibitor is used for SARS antiviral assays. Subconfluent cultures of cells are plated into 96-well plates for the analysis of cell viability (cytotoxicity) and antiviral activity (CPE). For the standard assay, drugs are added to the cells 24 hours later. The CPE wells also received 100 tissue culture infectious doses (100 $TCID_{50}$s) of titered virus. 72 hours later the cell viability will be determined. Measurement of viral-induced CPE is based on quantitation of ATP, an indicator of metabolically active cells. The CPE assay employs a commercially available CellTiter-Glo® Luminescent Cell Viability Kit (Promega, Madison, Wis.), and is a reliable method for determining cytotoxicity and cell proliferation in culture. The procedure involves adding the single reagent (CellTiter-Glo Reagent) directly to previously cultured, subconfluent cells in media. This induces cell lysis and the production of a bioluminescent signal (half-life greater than 5 hours, depending on the cell type) that is proportional to the amount of ATP present (which is a biomarker for viability).

As disclosed throughout, for example in FIGS. 4A, 4B, 6A, 6B, 6C, 7, and Table 4 Amodiaquine (AQ) and N-Desethyl Amodiaquine (DEAQ) inhibit cathepsin B dependent pathogens, thereby providing a method for treating subjects infected with these pathogens.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of inhibiting *Bacillus anthracis* in a host cell or in a subject, the method comprising;

administering Amodiaquine (AQ) or N-Desethyl Amodiaquine (DEAQ) to the host cell or the subject.

2. The method of claim 1, wherein the AQ or DEAQ is administered at a dose of about 4.2 uM to about 70 uM or about 1.5 mg/kg to about 10.0 mg/kg based on the weight of the subject.

3. The method of claim 1, further comprising administering an antibiotic.

4. The method of claim 3, wherein the antibiotic is selected from the group consisting of Octodrine, vancomycin, clindamycin, cephaloridine, fidaxomicin, metronidazole, ciprofloxacin, doxycycline, erythromycin, penicillin, tetracycline, and combinations thereof.

5. The method of claim 3, wherein the antibiotic comprises Octodrine.

6. The method of claim 3, wherein the antibiotic and the AQ or DEAQ are administered as a mixture.

7. The method of claim 5, wherein the AQ or DEAQ is administered at a dose of about 1.5 mg/kg to about 10.0 mg/kg and the Octodrine is administered at a dose of about 1.5 mg/kg to about 50 mg/kg based on the weight of the subject.

* * * * *